US011111503B2

(12) United States Patent
Saito et al.

(10) Patent No.: US 11,111,503 B2
(45) Date of Patent: Sep. 7, 2021

(54) METHOD FOR EXPRESSING PROTEIN GENE IN RESPONSE TO EXPRESSION OF MIRNA

(71) Applicant: KYOTO UNIVERSITY, Kyoto (JP)

(72) Inventors: Hirohide Saito, Kyoto (JP); Yoshihiko Fujita, Kyoto (JP)

(73) Assignee: Kyoto University, Kyoto (JP)

( * ) Notice: Subject to any disclaimer, the term of this patent is extended or adjusted under 35 U.S.C. 154(b) by 456 days.

(21) Appl. No.: 16/313,322

(22) PCT Filed: Jun. 27, 2017

(86) PCT No.: PCT/JP2017/023513
§ 371 (c)(1),
(2) Date: Apr. 10, 2019

(87) PCT Pub. No.: WO2018/003779
PCT Pub. Date: Jan. 4, 2018

(65) Prior Publication Data
US 2019/0256866 A1 Aug. 22, 2019

(30) Foreign Application Priority Data
Jun. 27, 2016 (JP) ............................ JP2016-126982

(51) Int. Cl.

| | |
|---|---|
| ***C12N 15/85*** | (2006.01) |
| ***C12N 15/09*** | (2006.01) |
| ***C12Q 1/68*** | (2018.01) |
| ***C12N 5/10*** | (2006.01) |

(52) U.S. Cl.
CPC ............. *C12N 15/85* (2013.01); *C12N 15/09* (2013.01); *C12N 5/10* (2013.01); *C12N 2840/102* (2013.01); *C12Q 1/68* (2013.01)

(58) Field of Classification Search
CPC .......... C12N 15/85; C12N 15/09; C12N 5/10; C12N 2840/102; C12N 15/63; C12N 15/67; C12Q 1/68
See application file for complete search history.

(56) References Cited

U.S. PATENT DOCUMENTS

| | | | |
|---|---|---|---|
| 2010/0323356 A1 | 12/2010 | Inoue et al. |
| 2014/0189895 A1 | 7/2014 | Wada et al. |
| 2017/0016077 A1 | 1/2017 | Saito et al. |

FOREIGN PATENT DOCUMENTS

| | | |
|---|---|---|
| WO | 2009/066758 | 5/2009 |
| WO | 2013/015152 | 1/2013 |
| WO | 2015/105172 | 7/2015 |

OTHER PUBLICATIONS

International Search Report and Written Opinion corresponding to International Application No. PCT/JP2017/023513 dated Oct. 3, 2017.
Matsuura et al. "Toward the Development of RNA-responsive ON Switch Functioning within Human Celis", The RNA Society of Japan Nenkai Yoshishu p. 237 (2015).
Miki et al, "Efficient Detection and Purification of Cell Populations Using Synthetic MicroRNA Switches", Cell Stem Cell 16:699-711 (2015).
Nakanishi et al. "Continuous microRNA detection by novel reporter vectors enable monitoring of iPS cell differentiation", Joint Meeting of the 38th Annual Meeting of the Molecular Biology Society of Japan and the 88th Annual Meeting of the Japanese Biochemical Society Koen Yoshishu (2015) 1T17 p. 12 (1PO966), entire text.
Rinaudo et al. "A universal RNAi-based logic evaluator that operates in mammalian cells", Nature Biotechnology 25(7):795-801 (2007).

*Primary Examiner* — Richard A Schnizer
(74) *Attorney, Agent, or Firm* — Myers Bigel, P.A.

(57) ABSTRACT

An mRNA forcibly expresses a protein gene in response to a miRNA, and a method for forcibly expressing the same, are provided. An artificial mRNA comprising a sequence encoding a protein gene, a miRNA target sequence linked to the 3'-terminal side of a Poly A sequence, and a translational repression sequence linked to the 3'-terminal side of the miRNA target sequence; and a method for expressing a protein gene in response to the expression of a miRNA, comprising a step of introducing the artificial mRNA into a cell.

19 Claims, 6 Drawing Sheets

Specification includes a Sequence Listing.

SEQUENCE LISTING

<160> NUMBER OF SEQ ID NOS: 52

<210> SEQ ID NO 1
<211> LENGTH: 45
<212> TYPE: DNA
<213> ORGANISM: Artificial Sequence
<220> FEATURE:
<223> OTHER INFORMATION: TAP_IVTrev

<400> SEQUENCE: 1
gccccgcaga aggtctagac tatcactcga gatgcatatg agatc 45

<210> SEQ ID NO 2
<211> LENGTH: 35
<212> TYPE: DNA
<213> ORGANISM: Artificial Sequence
<220> FEATURE:
<223> OTHER INFORMATION: TAPEGFP_IVTfwd

<400> SEQUENCE: 2
caccggtcgc caccatggga tccgtgagca agggc 35

<210> SEQ ID NO 3
<211> LENGTH: 87
<212> TYPE: DNA
<213> ORGANISM: Artificial Sequence
<220> FEATURE:
<223> OTHER INFORMATION: IVT_5prime_UTR

<400> SEQUENCE: 3
cagtgaattg taatacgact cactataggg cgaattaaga gagaaaagaa gagtaagaag 60
aaatataaga caccggtcgc caccatg 87

<210> SEQ ID NO 4
<211> LENGTH: 37
<212> TYPE: DNA
<213> ORGANISM: Artificial Sequence
<220> FEATURE:
<223> OTHER INFORMATION: Rev5UTR

<400> SEQUENCE: 4
catggtggcg accggtgtct tatatttctt cttactc 37

<210> SEQ ID NO 5
<211> LENGTH: 92
<212> TYPE: DNA
<213> ORGANISM: Artificial Sequence
<220> FEATURE:
<223> OTHER INFORMATION: IVT_3prime_UTR

<400> SEQUENCE: 5
tctagacctt ctgcggggct tgccttctgg ccatgccctt cttctctccc ttgcacctgt 60
acctcttggt ctttgaataa agcctgagta gg 92

<210> SEQ ID NO 6
<211> LENGTH: 48
<212> TYPE: DNA
<213> ORGANISM: Artificial Sequence
<220> FEATURE:
<223> OTHER INFORMATION: Rev3UTR2T20

<400> SEQUENCE: 6
tttttttttt tttttttttt cctactcagg ctttattcaa agaccaag 48

<210> SEQ ID NO 7
<211> LENGTH: 31
<212> TYPE: DNA
<213> ORGANISM: Artificial Sequence
<220> FEATURE:
<223> OTHER INFORMATION: TAP_T7_G3C_fwd_primer

<400> SEQUENCE: 7
cagtgaattg taatacgact cactataggg c 31

<210> SEQ ID NO 8
<211> LENGTH: 28
<212> TYPE: DNA
<213> ORGANISM: Artificial Sequence
<220> FEATURE:
<223> OTHER INFORMATION: Rev3UTR2

<400> SEQUENCE: 8
cctactcagg ctttattcaa agaccaag 28

<210> SEQ ID NO 9
<211> LENGTH: 150
<212> TYPE: DNA
<213> ORGANISM: Artificial Sequence
<220> FEATURE:
<223> OTHER INFORMATION: 3UTR-109A-Tg21

<400> SEQUENCE: 9
tagcttatca gactgatgtt gaattttttt tttttttttt tttttttttt tttttttttt 60
tttttttttt tttttttttt tttttttttt tttttttttt tttttttttt tttttttttt 120
tttttttttt ttcctactca ggctttattc 150

<210> SEQ ID NO 10
<211> LENGTH: 150
<212> TYPE: DNA
<213> ORGANISM: Artificial Sequence
<220> FEATURE:
<223> OTHER INFORMATION: 3UTR-109A-Tg302

<400> SEQUENCE: 10
acttaaacgt ggatgtactt gctttttttt tttttttttt tttttttttt tttttttttt 60
tttttttttt tttttttttt tttttttttt tttttttttt tttttttttt tttttttttt 120
tttttttttt ttcctactca ggctttattc 150

<210> SEQ ID NO 11
<211> LENGTH: 150
<212> TYPE: DNA
<213> ORGANISM: Artificial Sequence
<220> FEATURE:
<223> OTHER INFORMATION: 3UTR-109A-N

<400> SEQUENCE: 11
gttgcgatta tgaacctatt agattttttt tttttttttt tttttttttt tttttttttt 60
tttttttttt tttttttttt tttttttttt tttttttttt tttttttttt tttttttttt 120
tttttttttt ttcctactca ggctttattc 150

-continued

<210> SEQ ID NO 12
<211> LENGTH: 135
<212> TYPE: DNA
<213> ORGANISM: Artificial Sequence
<220> FEATURE:
<223> OTHER INFORMATION: Tg21-M13NRev

<400> SEQUENCE: 12
tgtggaattg tgagcggata acaatttcac acaggaaaca gctatgacca tgattacgcc 60
aagcttgcat gcctgcaggt cgactctaga ggatccccgg gtaccggtct cttagcttat 120
cagactgatg ttgaa 135

<210> SEQ ID NO 13
<211> LENGTH: 135
<212> TYPE: DNA
<213> ORGANISM: Artificial Sequence
<220> FEATURE:
<223> OTHER INFORMATION: N-M13NRev

<400> SEQUENCE: 13
tgtggaattg tgagcggata acaatttcac acaggaaaca gctatgacca tgattacgcc 60
aagcttgcat gcctgcaggt cgactctaga ggatccccgg gtaccggtct ctgttgcgat 120
tatgaaccta ttaga 135

<210> SEQ ID NO 14
<211> LENGTH: 51
<212> TYPE: DNA
<213> ORGANISM: Artificial Sequence
<220> FEATURE:
<223> OTHER INFORMATION: Tg21-M13Rev

<400> SEQUENCE: 14
cacacaggaa acagctatga ccatgtagct tatcagactg atgttgaatt t 51

<210> SEQ ID NO 15
<211> LENGTH: 51
<212> TYPE: DNA
<213> ORGANISM: Artificial Sequence
<220> FEATURE:
<223> OTHER INFORMATION: N-M13Rev

<400> SEQUENCE: 15
cacacaggaa acagctatga ccatggttgc gattatgaac ctattagatt t 51

<210> SEQ ID NO 16
<211> LENGTH: 51
<212> TYPE: DNA
<213> ORGANISM: Artificial Sequence
<220> FEATURE:
<223> OTHER INFORMATION: Tg302-M13Rev

<400> SEQUENCE: 16
cacacaggaa acagctatga ccatgactta aacgtggatg tacttgcttt t 51

<210> SEQ ID NO 17
<211> LENGTH: 51
<212> TYPE: DNA
<213> ORGANISM: Artificial Sequence
<220> FEATURE:
<223> OTHER INFORMATION: Tg21-Rn2-Rev

<400> SEQUENCE: 17
gttacattgt gccacggagt cgatctagct tatcagactg atgttgaatt t 51

<210> SEQ ID NO 18
<211> LENGTH: 51
<212> TYPE: DNA
<213> ORGANISM: Artificial Sequence
<220> FEATURE:
<223> OTHER INFORMATION: Tg302-Rn2-Rev

<400> SEQUENCE: 18
gttacattgt gccacggagt cgatcactta aacgtggatg tacttgcttt t 51

<210> SEQ ID NO 19
<211> LENGTH: 77
<212> TYPE: DNA
<213> ORGANISM: Artificial Sequence
<220> FEATURE:
<223> OTHER INFORMATION: YF549-M13-T20N20

<400> SEQUENCE: 19
tcttcgggct gcgagaattc aaaaaaaaaa aaaaaaaaaa aaaaaaaaaa aaaaaaaaaa 60
tgtggaattg tgagcgg 77

<210> SEQ ID NO 20
<211> LENGTH: 77
<212> TYPE: DNA
<213> ORGANISM: Artificial Sequence
<220> FEATURE:
<223> OTHER INFORMATION: YF550-M13-T40N20

<400> SEQUENCE: 20
tcttcgggct gcgagaattc aaaaaaaaaa aaaaaaaaaa aaaaaaaaaa aaaaaaaaaa 60
tgtggaattg tgagcgg 77

<210> SEQ ID NO 21
<211> LENGTH: 97
<212> TYPE: DNA
<213> ORGANISM: Artificial Sequence
<220> FEATURE:
<223> OTHER INFORMATION: YF551-M13-T60N20

<400> SEQUENCE: 21
tcttcgggct gcgagaattc aaaaaaaaaa aaaaaaaaaa aaaaaaaaaa aaaaaaaaaa 60
aaaaaaaaaa aaaaaaaaaa tgtggaattg tgagcgg 97

<210> SEQ ID NO 22
<211> LENGTH: 117
<212> TYPE: DNA
<213> ORGANISM: Artificial Sequence
<220> FEATURE:
<223> OTHER INFORMATION: YF552-M13-T80N20

<400> SEQUENCE: 22
tcttcgggct gcgagaattc aaaaaaaaaa aaaaaaaaaa aaaaaaaaaa aaaaaaaaaa 60
aaaaaaaaaa aaaaaaaaaa aaaaaaaaaa aaaaaaaaaa tgtggaattg tgagcgg 117

<210> SEQ ID NO 23
<211> LENGTH: 235
<212> TYPE: RNA
<213> ORGANISM: Artificial Sequence
<220> FEATURE:
<223> OTHER INFORMATION: Tg21-U80

<400> SEQUENCE: 23

-continued

```
uucaacauca gucugauaag cuaagagacc gguacccggg gauccucuag agucgaccug     60

caggcaugca agcuuggcgu aaucaugguc auagcuguuu ccugugugaa auuguuaucc    120

gcucacaauu ccacauuuuu uuuuuuuuuu uuuuuuuuuu uuuuuuuuuu uuuuuuuuuu    180

uuuuuuuuuu uuuuuuuuuu uuuuuuuuuu uuuuugaauu cucgcagccc gaaga         235
```

```
<210> SEQ ID NO 24
<211> LENGTH: 25
<212> TYPE: DNA
<213> ORGANISM: Artificial Sequence
<220> FEATURE:
<223> OTHER INFORMATION: M13Rev-Fwd

<400> SEQUENCE: 24

catggtcata gctgtttcct gtgtg                                           25
```

```
<210> SEQ ID NO 25
<211> LENGTH: 30
<212> TYPE: DNA
<213> ORGANISM: Artificial Sequence
<220> FEATURE:
<223> OTHER INFORMATION: M13Rev-1000-Rev

<400> SEQUENCE: 25

gcattggtaa ctgtcagacc aagtttactc                                      30
```

```
<210> SEQ ID NO 26
<211> LENGTH: 27
<212> TYPE: DNA
<213> ORGANISM: Artificial Sequence
<220> FEATURE:
<223> OTHER INFORMATION: M13Rev-500-Rev

<400> SEQUENCE: 26

ggagcctatg gaaaaacgcc agcaacg                                         27
```

```
<210> SEQ ID NO 27
<211> LENGTH: 518
<212> TYPE: RNA
<213> ORGANISM: Artificial Sequence
<220> FEATURE:
<223> OTHER INFORMATION: 500 nt

<400> SEQUENCE: 27

uucaacauca gucugauaag cuacaugguc auagcuguuu ccugugugaa auuguuaucc     60

gcucacaauu ccacacaaca uacgagccgg aagcauaaag uguaaagccu ggggugccua    120

augagugagc uaacucacau uaauugcguu gcgcucacug cccgcuuucc agucgggaaa    180

ccugucgugc cagcugcauu aaugaaucgg ccaacgcgcg gggagaggcg guuugcguau    240

ugggcgcucu uccgcuuccu cgcucacuga cucgcugcgc ucggucguuc ggcugcggcg    300

agcgguauca gcucacucaa aggcggucgc uuccucgcuc acugacucgc ugcgcucggu    360

cguucggcug cggcgagcgg uaucagcuca cucaaaggcg guaauacggu uauccacaga    420

aucaggggau aacgcaggaa agaacaugug agcaaaaggc cagcaaaagg ccaggaaccg    480

uaaaaaggcc gcguugcugg cguuuuucca uaggcucc                            518
```

```
<210> SEQ ID NO 28
<211> LENGTH: 1273
<212> TYPE: RNA
<213> ORGANISM: Artificial Sequence
<220> FEATURE:
<223> OTHER INFORMATION: 1200 nt
```

-continued

<400> SEQUENCE: 28

```
uucaacauca gucugauaag cuacaugguc auagcuguuu ccugugugaa auuguuaucc     60
gcucacaauu ccacacaaca uacgagccgg aagcauaaag uguaaagccu ggggugccua    120
augagugagc uaacucacau uaauugcguu gcgcucacug cccgcuuucc agucgggaaa    180
ccugucgugc cagcugcauu aaugaaucgg ccaacgcgcg gggagaggcg guuugcguau    240
ugggcgcucu uccgcuuccu cgcucacuga cucgcugcgc ucggucguuc ggcugcggcg    300
agcgguauca gcucacucaa aggcggucgc uuccucgcuc acugacucgc ugcgcucggu    360
cguucggcug cggcgagcgg uaucagcuca cucaaaggcg guaauacggu uauccacaga    420
aucaggggau aacgcaggaa agaacaugug agcaaaaggc cagcaaaagg ccaggaaccg    480
uaaaaaggcc gcguugcugg cguuuuucca uaggcuccgc cccccugacg agcaucacaa    540
aaaucgacgc ucaagucaga gguggcgaaa cccgacagga cuauaaagau accaggcguu    600
ucccccugga agcucccucg ugcgcucucc uguuccgacc cugccgcuua ccggauaccu    660
guccgccuuu cucccuucgg gaagcguggc gcuuucucau agcucacgcu guagguaucu    720
caguucggug uaggucguuc gcuccaagcu gggcugugug cacgaacccc ccguucagcc    780
cgaccgcugc gccuuauccg guaacuaucg ucuugagucc aacccgguaa gacacgacuu    840
aucgccacug gcagcagcca cugguaacag gauuagcaga gcgagguaug uaggcggugc    900
uacagaguuc uugaaguggu ggccuaacua cggcuacacu agaagaacag uauuugguau    960
cugcgcucug cugaagccag uuaccuucgg aaaaagaguu gguagcucuu gauccggcaa   1020
acaaaccacc gcugguagcg gugguuuuuu uguuugcaag cagcagauua cgcgcagaaa   1080
aaaaggaucu caagaagauc cuuugaucuu uucuacgggg ucugacgcuc aguggaacga   1140
aaacucacgu uaagggauuu uggucaugag auuaucaaaa aggaucuuca ccuagauccu   1200
uuuaaauuaa aaaugaaguu uuaaaucaau cuaaaguaua uaugaguaaa cuuggucuga   1260
caguuaccaa ugc                                                      1273
```

<210> SEQ ID NO 29
<211> LENGTH: 65
<212> TYPE: DNA
<213> ORGANISM: Artificial Sequence
<220> FEATURE:
<223> OTHER INFORMATION: M13Rev-5Cmp20N20

<400> SEQUENCE: 29

```
tcttcgggct gcgagaattc gggcgaatta agagagaaaa cacacaggaa acagctatga     60
ccatg                                                                 65
```

<210> SEQ ID NO 30
<211> LENGTH: 85
<212> TYPE: DNA
<213> ORGANISM: Artificial Sequence
<220> FEATURE:
<223> OTHER INFORMATION: M13Rev-5Cmp40N20

<400> SEQUENCE: 30

```
tcttcgggct gcgagaattc gggcgaatta agagagaaaa gaagagtaag aagaaatata     60
cacacaggaa acagctatga ccatg                                           85
```

<210> SEQ ID NO 31
<211> LENGTH: 89
<212> TYPE: DNA

-continued

<213> ORGANISM: Artificial Sequence
<220> FEATURE:
<223> OTHER INFORMATION: M13Rev-5Cmp20SLN20

<400> SEQUENCE: 31
tcttcgggct gcgagaattc cgcgctggac tcccgtccag cgcggggcga attaagagag 60
aaaacacaca ggaaacagct atgaccatg 89

<210> SEQ ID NO 32
<211> LENGTH: 108
<212> TYPE: RNA
<213> ORGANISM: Artificial Sequence
<220> FEATURE:
<223> OTHER INFORMATION: 5UTR_Comp40nt

<400> SEQUENCE: 32
uucaacauca gucugauaag cuacaugguc auagcuguuu ccugugugua uauuucuucu 60
uacucuucuu uucucucuua auucgcccga auucucgcag cccgaaga 108

<210> SEQ ID NO 33
<211> LENGTH: 88
<212> TYPE: RNA
<213> ORGANISM: Artificial Sequence
<220> FEATURE:
<223> OTHER INFORMATION: 5UTR_Comp20nt

<400> SEQUENCE: 33
uucaacauca gucugauaag cuacaugguc auagcuguuu ccuguguguu uucucucuua 60
auucgcccga auucucgcag cccgaaga 88

<210> SEQ ID NO 34
<211> LENGTH: 112
<212> TYPE: RNA
<213> ORGANISM: Artificial Sequence
<220> FEATURE:
<223> OTHER INFORMATION: 5UTR_Comp20nt_Stemloop

<400> SEQUENCE: 34
uucaacauca gucugauaag cuacaugguc auagcuguuu ccuguguguu uucucucuua 60
auucgccccg cgcuggacgg gaguccagcg cggaauucuc gcagcccgaa ga 112

<210> SEQ ID NO 35
<211> LENGTH: 1013
<212> TYPE: RNA
<213> ORGANISM: Artificial Sequence
<220> FEATURE:
<223> OTHER INFORMATION: miR21-responsive OFF switch EGFP mRNA

<400> SEQUENCE: 35
gguuccuuaa ucgcggaucc ucaacaucag ucugauaagc uaagaucaca ccggucgcca 60
ccaugggauc cgugagcaag ggcgaggagc uguucaccgg gguggugccc auccuggucg 120
agcuggacgg cgacguaaac ggccacaagu ucagcguguc cggcgagggc gagggcgaug 180
ccaccuacgg caagcugacc cugaaguuca ucugcaccac cggcaagcug cccgugcccu 240
ggcccacccu cgugaccacc cugaccuacg gcgugcagug cuucagccgc uaccccgacc 300
acaugaagca gcacgacuuc uucaaguccg ccaugcccga aggcuacguc caggagcgca 360
ccaucuucuu caaggacgac ggcaacuaca agacccgcgc cgaggugaag uucgagggcg 420
acacccuggu gaaccgcauc gagcugaagg gcaucgacuu caaggaggac ggcaacaucc 480
uggggcacaa gcuggaguac aacuacaaca gccacaacgu cuauaucaug gccgacaagc 540

-continued

```
agaagaacgg caucaaggug aacuucaaga uccgccacaa caucgaggac ggcagcgugc    600

agcucgccga ccacuaccag cagaacaccc ccaucggcga cggccccgug cugcugcccg    660

acaaccacua ccugagcacc caguccgccc ugagcaaaga ccccaacgag aagcgcgauc    720

acauggcccu gcuggaguuc gugaccgccg ccgggaucac ucucggcaug gacgagcugu    780

acaagagauc ucauaugcau cucgagugau agucuagacc uucugcgggg cuugccuucu    840

ggccaugccc uucuucucuc ccuugcaccu guaccucuug gucuuugaau aaagccugag    900

uaggaaaaaa aaaaaaaaaa aaaaaaaaaa aaaaaaaaaa aaaaaaaaaa aaaaaaaaaa    960

aaaaaaaaaa aaaaaaaaaa aaaaaaaaaa aaaaaaaaaa aaaaaaaaaa aaa          1013
```

<210> SEQ ID NO 36
<211> LENGTH: 1008
<212> TYPE: RNA
<213> ORGANISM: Artificial Sequence
<220> FEATURE:
<223> OTHER INFORMATION: Control EGFP mRNA

<400> SEQUENCE: 36

```
gggcgaauua agagagaaaa gaagaguaag aagaaauaua agacaccggu cgccaccaug     60

ggauccguga gcaagggcga ggagcuguuc accggggugg ugcccauccu ggucgagcug    120

gacggcgacg uaaacggcca caaguucagc guguccggcg agggcgaggg cgaugccacc    180

uacggcaagc ugacccugaa guucaucugc accaccggca agcugcccgu gcccuggccc    240

acccucguga ccacccugac cuacggcgug cagugcuuca gccgcuaccc cgaccacaug    300

aagcagcacg acuucuucaa guccgccaug cccgaaggcu acguccagga gcgcaccauc    360

uucuucaagg acgacggcaa cuacaagacc cgcgccgagg ugaaguucga gggcgacacc    420

cuggugaacc gcaucgagcu gaagggcauc gacuucaagg aggacggcaa cauccugggg    480

cacaagcugg aguacaacua caacagccac aacgucuaua ucauggccga caagcagaag    540

aacggcauca aggugaacuu caagauccgc cacaacaucg aggacggcag cgugcagcuc    600

gccgaccacu accagcagaa cacccccauc ggcgacggcc ccgugcugcu gcccgacaac    660

cacuaccuga gcacccaguc cgcccugagc aaagacccca acgagaagcg cgaucacaug    720

guccugcugg aguucgugac cgccgccggg aucacucucg gcauggacga gcuguacaag    780

agaucucaua ugcaucucga gugauagucu agaccuucug cggggcuugc cuucuggcca    840

ugcccuucuu cucucccuug caccuguacc ucuuggucuu ugaauaaagc cugaguagga    900

aaaaaaaaaa aaaaaaaaaa aaaaaaaaaa aaaaaaaaaa aaaaaaaaaa aaaaaaaaaa    960

aaaaaaaaaa aaaaaaaaaa aaaaaaaaaa aaaaaaaaaa aaaaaaaa                1008
```

<210> SEQ ID NO 37
<211> LENGTH: 1218
<212> TYPE: RNA
<213> ORGANISM: Artificial Sequence
<220> FEATURE:
<223> OTHER INFORMATION: Control iRFP670 mRNA

<400> SEQUENCE: 37

```
gggcgaauua agagagaaaa gaagaguaag aagaaauaua agacaccggu cgccaccaug     60

gcgcguaagg ucgaucucac cuccugcgau cgcgagccga uccacauccc cggcagcauu    120

cagccgugcg gcugccugcu agccugcgac gcgcaggcgg ugcggaucac gcgcauuacg    180

gaaaaugccg gcgcguucuu uggacgcgaa acuccgcggg ucggugagcu acucgccgau    240
```

-continued

```
uacuucggcg agaccgaagc ccaugcgcug cgcaacgcac uggcgcaguc cuccgaucca    300

aagcgaccgg cgcugaucuu cgguuggcgc gacggccuga ccggccgcac cuucgacauc    360

ucacugcauc gccaugacgg uacaucgauc aucgaguucg agccugcggc ggccgaacag    420

gccgacaauc cgcugcggcu gacgcggcag aucaucgcgc gcaccaaaga acugaagucg    480

cucgaagaga uggccgcacg ggugccgcgc uaucugcagg cgaugcucgg cuaucaccgc    540

gugauguugu accgcuucgc ggacgacggc uccgggaugg ugaucggcga ggcgaagcgc    600

agcgaccucg agagcuuucu cggucagcac uuuccggcgu cgcugguccc gcagcaggcg    660

cggcuacugu acuugaagaa cgcgauccgc guggucucgg auucgcgcgg caucagcagc    720

cggaucgugc ccgagcacga cgccuccggc gccgcgcucg aucugucguu cgcgcaccug    780

cgcagcaucu cgcccugcca ucucgaauuu cugcggaaca ugggcgucag cgccucgaug    840

ucgcugucga ucaucauuga cggcacgcua uggggauuga ucaucuguca ucauuacgag    900

ccgcgugccg ugccgauggc gcagcgcguc gcggccgaaa uguucgccga cuucuuaucg    960

cugcacuuca ccgccgccca ccaccaacgc agaucucaua ugcaucucga gugauagucu   1020

agaccuucug cggggcuugc cuucuggcca ugcccuucuu cucucccuug caccuguacc   1080

ucuuggucuu ugaauaaagc cugaguagga aaaaaaaaaa aaaaaaaaaa aaaaaaaaaa   1140

aaaaaaaaaa aaaaaaaaaa aaaaaaaaaa aaaaaaaaaa aaaaaaaaaa aaaaaaaaaa   1200

aaaaaaaaaa aaaaaaaa                                                 1218
```

<210> SEQ ID NO 38
<211> LENGTH: 1243
<212> TYPE: RNA
<213> ORGANISM: Artificial Sequence
<220> FEATURE:
<223> OTHER INFORMATION: EGFP-A109-Tg21-U80

<400> SEQUENCE: 38

```
gggcgaauua agagagaaaa gaagaguaag aagaaauaua agacaccggu cgccaccaug     60

ggauccguga gcaagggcga ggagcuguuc accggggugg ugcccauccu ggucgagcug    120

gacggcgacg uaaacggcca caaguucagc guguccggcg agggcgaggg cgaugccacc    180

uacggcaagc ugacccugaa guucaucugc accaccggca agcugcccgu gcccuggccc    240

acccucguga ccacccugac cuacggcgug cagugcuuca gccgcuaccc cgaccacaug    300

aagcagcacg acuucuucaa guccgccaug cccgaaggcu acguccagga gcgcaccauc    360

uucuucaagg acgacggcaa cuacaagacc cgcgccgagg ugaaguucga gggcgacacc    420

cuggugaacc gcaucgagcu gaagggcauc gacuucaagg aggacggcaa cauccugggg    480

cacaagcugg aguacaacua caacagccac aacgucuaua ucauggccga caagcagaag    540

aacggcauca aggugaacuu caagauccgc cacaacaucg aggacggcag cgugcagcuc    600

gccgaccacu accagcagaa cacccccauc ggcgacggcc ccgugcugcu gcccgacaac    660

cacuaccuga gcacccaguc cgcccugagc aaagaccccca acgagaagcg cgaucacaug    720

guccugcugg aguucgugac cgccgccggg aucacucucg gcauggacga gcuguacaag    780

agaucucaua ugcaucucga gugauagucu agaccuucug cggggcuugc cuucuggcca    840

ugcccuucuu cucucccuug caccuguacc ucuuggucuu ugaauaaagc cugaguagga    900

aaaaaaaaaa aaaaaaaaaa aaaaaaaaaa aaaaaaaaaa aaaaaaaaaa aaaaaaaaaa    960

aaaaaaaaaa aaaaaaaaaa aaaaaaaaaa aaaaaaaaaa aaaaaaaauu caacaucagu   1020

cugauaagcu aagagaccgg uacccgggga uccucuagag ucgaccugca ggcaugcaag   1080
```

-continued

```
cuuggcguaa ucauggucau agcuguuucc ugugugaaau uguuauccgc ucacaauucc   1140

acauuuuuuu uuuuuuuuuu uuuuuuuuuu uuuuuuuuuu uuuuuuuuuu uuuuuuuuuu   1200

uuuuuuuuuu uuuuuuuuuu uuugaauucu cgcagcccga aga                     1243
```

```
<210> SEQ ID NO 39
<211> LENGTH: 1223
<212> TYPE: RNA
<213> ORGANISM: Artificial Sequence
<220> FEATURE:
<223> OTHER INFORMATION: EGFP-A109-Tg21-U60

<400> SEQUENCE: 39

gggcgaauua agagagaaaa gaagaguaag aagaaauaua agacaccggu cgccaccaug     60

ggauccguga gcaagggcga ggagcuguuc accggggugg ugcccauccu ggucgagcug    120

gacggcgacg uaaacggcca caaguucagc guguccggcg agggcgaggg cgaugccacc    180

uacggcaagc ugacccugaa guucaucugc accaccggca agcugcccgu gcccuggccc    240

acccucguga ccacccugac cuacggcgug cagugcuuca gccgcuaccc cgaccacaug    300

aagcagcacg acuucuucaa guccgccaug cccgaaggcu acguccagga gcgcaccauc    360

uucuucaagg acgacggcaa cuacaagacc cgcgccgagg ugaaguucga gggcgacacc    420

cuggugaacc gcaucgagcu gaagggcauc gacuucaagg aggacggcaa cauccugggg    480

cacaagcugg aguacaacua caacagccac aacgucuaua ucauggccga caagcagaag    540

aacggcauca aggugaacuu caagauccgc cacaacaucg aggacggcag cgugcagcuc    600

gccgaccacu accagcagaa cacccccauc ggcgacggcc ccgugcugcu gcccgacaac    660

cacuaccuga gcacccaguc cgcccugagc aaagacccca acgagaagcg cgaucacaug    720

guccugcugg aguucgugac cgccgccggg aucacucucg gcauggacga gcuguacaag    780

agaucucaua ugcaucucga gugauagucu agaccuucug cggggcuugc cuucuggcca    840

ugcccuucuu cucucccuug caccuguacc ucuuggucuu ugaauaaagc cugaguagga    900

aaaaaaaaaa aaaaaaaaaa aaaaaaaaaa aaaaaaaaaa aaaaaaaaaa aaaaaaaaaa    960

aaaaaaaaaa aaaaaaaaaa aaaaaaaaaa aaaaaaaaaa aaaaaaaauu caacaucagu   1020

cugauaagcu aagagaccgg uacccgggga uccucuagag ucgaccugca ggcaugcaag   1080

cuuggcguaa ucauggucau agcuguuucc ugugugaaau uguuauccgc ucacaauucc   1140

acauuuuuuu uuuuuuuuuu uuuuuuuuuu uuuuuuuuuu uuuuuuuuuu uuuuuuuuuu   1200

uuugaauucu cgcagcccga aga                                           1223
```

```
<210> SEQ ID NO 40
<211> LENGTH: 1203
<212> TYPE: RNA
<213> ORGANISM: Artificial Sequence
<220> FEATURE:
<223> OTHER INFORMATION: EGFP-A109-Tg21-U40

<400> SEQUENCE: 40

gggcgaauua agagagaaaa gaagaguaag aagaaauaua agacaccggu cgccaccaug     60

ggauccguga gcaagggcga ggagcuguuc accggggugg ugcccauccu ggucgagcug    120

gacggcgacg uaaacggcca caaguucagc guguccggcg agggcgaggg cgaugccacc    180

uacggcaagc ugacccugaa guucaucugc accaccggca agcugcccgu gcccuggccc    240

acccucguga ccacccugac cuacggcgug cagugcuuca gccgcuaccc cgaccacaug    300
```

aagcagcacg acuucuucaa guccgccaug cccgaaggcu acguccagga gcgcaccauc 360
uucuucaagg acgacggcaa cuacaagacc cgcgccgagg ugaaguucga gggcgacacc 420
cuggugaacc gcaucgagcu gaagggcauc gacuucaagg aggacggcaa cauccugggg 480
cacaagcugg aguacaacua caacagccac aacgucuaua ucauggccga caagcagaag 540
aacggcauca aggugaacuu caagauccgc cacaacaucg aggacggcag cgugcagcuc 600
gccgaccacu accagcagaa cacccccauc ggcgacggcc ccgugcugcu gcccgacaac 660
cacuaccuga gcacccaguc cgcccugagc aaagacccca acgagaagcg cgaucacaug 720
guccugcugg aguucgugac cgccgccggg aucacucucg gcauggacga gcuguacaag 780
agaucucaua ugcaucucga gugauagucu agaccuucug cggggcuugc cuucuggcca 840
ugcccuucuu cucucccuug caccuguacc ucuuggucuu ugaauaaagc cugaguagga 900
aaaaaaaaaa aaaaaaaaaa aaaaaaaaaa aaaaaaaaaa aaaaaaaaaa aaaaaaaaaa 960
aaaaaaaaaa aaaaaaaaaa aaaaaaaaaa aaaaaaaaaa aaaaaaaauu caacaucagu 1020
cugauaagcu aagagaccgg uacccgggga ucccuagag ucgaccugca ggcaugcaag 1080
cuuggcguaa ucauggucau agcuguuucc ugugugaaau uguuauccgc ucacaauucc 1140
acauuuuuuu uuuuuuuuuu uuuuuuuuuu uuuuuuuuuu uuugaauucu cgcagcccga 1200
aga 1203

<210> SEQ ID NO 41
<211> LENGTH: 1183
<212> TYPE: RNA
<213> ORGANISM: Artificial Sequence
<220> FEATURE:
<223> OTHER INFORMATION: EGFP-A109-Tg21-U20

<400> SEQUENCE: 41
gggcgaauua agagagaaaa gaagaguaag aagaaauaua agacaccggu cgccaccaug 60
ggauccguga gcaagggcga ggagcuguuc accggggugg ugcccauccu ggucgagcug 120
gacggcgacg uaaacggcca caaguucagc guguccggcg agggcgaggg cgaugccacc 180
uacggcaagc ugacccugaa guucaucugc accaccggca agcugcccgu gcccuggccc 240
acccucguga ccacccugac cuacggcgug cagugcuuca gccgcuaccc cgaccacaug 300
aagcagcacg acuucuucaa guccgccaug cccgaaggcu acguccagga gcgcaccauc 360
uucuucaagg acgacggcaa cuacaagacc cgcgccgagg ugaaguucga gggcgacacc 420
cuggugaacc gcaucgagcu gaagggcauc gacuucaagg aggacggcaa cauccugggg 480
cacaagcugg aguacaacua caacagccac aacgucuaua ucauggccga caagcagaag 540
aacggcauca aggugaacuu caagauccgc cacaacaucg aggacggcag cgugcagcuc 600
gccgaccacu accagcagaa cacccccauc ggcgacggcc ccgugcugcu gcccgacaac 660
cacuaccuga gcacccaguc cgcccugagc aaagacccca acgagaagcg cgaucacaug 720
guccugcugg aguucgugac cgccgccggg aucacucucg gcauggacga gcuguacaag 780
agaucucaua ugcaucucga gugauagucu agaccuucug cggggcuugc cuucuggcca 840
ugcccuucuu cucucccuug caccuguacc ucuuggucuu ugaauaaagc cugaguagga 900
aaaaaaaaaa aaaaaaaaaa aaaaaaaaaa aaaaaaaaaa aaaaaaaaaa aaaaaaaaaa 960
aaaaaaaaaa aaaaaaaaaa aaaaaaaaaa aaaaaaaaaa aaaaaaaauu caacaucagu 1020
cugauaagcu aagagaccgg uacccgggga uccucuagag ucgaccugca ggcaugcaag 1080
cuuggcguaa ucauggucau agcuguuucc ugugugaaau uguuauccgc ucacaauucc 1140
acauuuuuuu uuuuuuuuuu uuugaauucu cgcagcccga aga 1183

<210> SEQ ID NO 42
<211> LENGTH: 1243
<212> TYPE: RNA
<213> ORGANISM: Artificial Sequence
<220> FEATURE:
<223> OTHER INFORMATION: EGFP-A109-N-U80

<400> SEQUENCE: 42
gggcgaauua agagagaaaa gaagaguaag aagaaauaua agacaccggu cgccaccaug 60
ggauccguga gcaagggcga ggagcuguuc accggggugg ugcccauccu ggucgagcug 120
gacggcgacg uaaacggcca caaguucagc guguccggcg agggcgaggg cgaugccacc 180
uacggcaagc ugacccugaa guucaucugc accaccggca agcugcccgu gcccuggccc 240
acccucguga ccacccugac cuacggcgug cagugcuuca gccgcuaccc cgaccacaug 300
aagcagcacg acuucuucaa guccgccaug cccgaaggcu acguccagga gcgcaccauc 360
uucuucaagg acgacggcaa cuacaagacc cgcgccgagg ugaaguucga gggcgacacc 420
cuggugaacc gcaucgagcu gaagggcauc gacuucaagg aggacggcaa cauccugggg 480
cacaagcugg aguacaacua caacagccac aacgucuaua ucauggccga caagcagaag 540
aacggcauca aggugaacuu caagauccgc cacaacaucg aggacggcag cgugcagcuc 600
gccgaccacu accagcagaa cacccccauc ggcgacggcc ccgugcugcu gcccgacaac 660
cacuaccuga gcacccaguc cgcccugagc aaagacccca acgagaagcg cgaucacaug 720
guccugcugg aguucgugac cgccgccggg aucacucucg gcauggacga gcuguacaag 780
agaucucaua ugcaucucga gugauagucu agaccuucug cggggcuugc cuucuggcca 840
ugcccuucuu cucucccuug caccuguacc ucuuggucuu ugaauaaagc cugaguagga 900
aaaaaaaaaa aaaaaaaaaa aaaaaaaaaa aaaaaaaaaa aaaaaaaaaa aaaaaaaaaa 960
aaaaaaaaaa aaaaaaaaaa aaaaaaaaaa aaaaaaaaaa aaaaaaaaug uugcgauuau 1020
gaaccuauua gagagaccgg uacccgggga uccucuagag ucgaccugca ggcaugcaag 1080
cuuggcguaa ucauggucau agcuguuucc ugugugaaau uguuauccgc ucacaauucc 1140
acauuuuuuu uuuuuuuuuu uuuuuuuuuu uuuuuuuuuu uuuuuuuuuu uuuuuuuuuu 1200
uuuuuuuuuu uuuuuuuuuu uuugaauucu cgcagcccga aga 1243

<210> SEQ ID NO 43
<211> LENGTH: 1223
<212> TYPE: RNA
<213> ORGANISM: Artificial Sequence
<220> FEATURE:
<223> OTHER INFORMATION: EGFP-A109-N-U60

<400> SEQUENCE: 43
gggcgaauua agagagaaaa gaagaguaag aagaaauaua agacaccggu cgccaccaug 60
ggauccguga gcaagggcga ggagcuguuc accggggugg ugcccauccu ggucgagcug 120
gacggcgacg uaaacggcca caaguucagc guguccggcg agggcgaggg cgaugccacc 180
uacggcaagc ugacccugaa guucaucugc accaccggca agcugcccgu gcccuggccc 240
acccucguga ccacccugac cuacggcgug cagugcuuca gccgcuaccc cgaccacaug 300
aagcagcacg acuucuucaa guccgccaug cccgaaggcu acguccagga gcgcaccauc 360
uucuucaagg acgacggcaa cuacaagacc cgcgccgagg ugaaguucga gggcgacacc 420

-continued cuggugaacc gcaucgagcu gaagggcauc gacuucaagg aggacggcaa cauccugggg 480
cacaagcugg aguacaacua caacagccac aacgucuaua ucauggccga caagcagaag 540
aacggcauca aggugaacuu caagauccgc cacaacaucg aggacggcag cgugcagcuc 600
gccgaccacu accagcagaa cacccccauc ggcgacggcc ccgugcugcu gcccgacaac 660
cacuaccuga gcacccaguc cgcccugagc aaagacccca acgagaagcg cgaucacaug 720
guccugcugg aguucgugac cgccgccggg aucacucucg gcauggacga gcuguacaag 780
agaucucaua ugcaucucga gugauagucu agaccuucug cggggcuugc cuucuggcca 840
ugcccuucuu cucucccuug caccuguacc ucuuggucuu ugaauaaagc cugaguagga 900
aaaaaaaaaa aaaaaaaaaa aaaaaaaaaa aaaaaaaaaa aaaaaaaaaa aaaaaaaaaa 960
aaaaaaaaaa aaaaaaaaaa aaaaaaaaaa aaaaaaaaaa aaaaaaaaug uugcgauuau 1020
gaaccuauua gagagaccgg uacccgggga uccucuagag ucgaccugca ggcaugcaag 1080
cuuggcguaa ucauggucau agcuguuucc ugugugaaau uguuauccgc ucacaauucc 1140
acauuuuuuu uuuuuuuuuu uuuuuuuuuu uuuuuuuuuu uuuuuuuuuu uuuuuuuuuu 1200
uuugaauucu cgcagcccga aga 1223

<210> SEQ ID NO 44
<211> LENGTH: 1203
<212> TYPE: RNA
<213> ORGANISM: Artificial Sequence
<220> FEATURE:
<223> OTHER INFORMATION: EGFP-A109-N-U40

<400> SEQUENCE: 44
gggcgaauua agagagaaaa gaagaguaag aagaaauaua agacaccggu cgccaccaug 60
ggauccguga gcaagggcga ggagcuguuc accgggguggg ugcccauccu ggucgagcug 120
gacggcgacg uaaacggcca caaguucagc guguccggcg agggcgaggg cgaugccacc 180
uacggcaagc ugacccugaa guucaucugc accaccggca agcugcccgu gcccuggccc 240
acccucguga ccacccugac cuacggcgug cagugcuuca gccgcuaccc cgaccacaug 300
aagcagcacg acuucuucaa guccgccaug cccgaaggcu acguccagga gcgcaccauc 360
uucuucaagg acgacggcaa cuacaagacc cgcgccgagg ugaaguucga gggcgacacc 420
cuggugaacc gcaucgagcu gaagggcauc gacuucaagg aggacggcaa cauccugggg 480
cacaagcugg aguacaacua caacagccac aacgucuaua ucauggccga caagcagaag 540
aacggcauca aggugaacuu caagauccgc cacaacaucg aggacggcag cgugcagcuc 600
gccgaccacu accagcagaa cacccccauc ggcgacggcc ccgugcugcu gcccgacaac 660
cacuaccuga gcacccaguc cgcccugagc aaagacccca acgagaagcg cgaucacaug 720
guccugcugg aguucgugac cgccgccggg aucacucucg gcauggacga gcuguacaag 780
agaucucaua ugcaucucga gugauagucu agaccuucug cggggcuugc cuucuggcca 840
ugcccuucuu cucucccuug caccuguacc ucuuggucuu ugaauaaagc cugaguagga 900
aaaaaaaaaa aaaaaaaaaa aaaaaaaaaa aaaaaaaaaa aaaaaaaaaa aaaaaaaaaa 960
aaaaaaaaaa aaaaaaaaaa aaaaaaaaaa aaaaaaaaaa aaaaaaaaug uugcgauuau 1020
gaaccuauua gagagaccgg uacccgggga uccucuagag ucgaccugca ggcaugcaag 1080
cuuggcguaa ucauggucau agcuguuucc ugugugaaau uguuauccgc ucacaauucc 1140
acauuuuuuu uuuuuuuuuu uuuuuuuuuu uuuuuuuuuu uuugaauucu cgcagcccga 1200
aga 1203

<210> SEQ ID NO 45
<211> LENGTH: 1183
<212> TYPE: RNA
<213> ORGANISM: Artificial Sequence
<220> FEATURE:
<223> OTHER INFORMATION: EGFP-A109-N-U20

<400> SEQUENCE: 45
gggcgaauua agagagaaaa gaagaguaag aagaaauaua agacaccggu cgccaccaug 60
ggauccguga gcaagggcga ggagcuguuc accggggugg ugcccauccu ggucgagcug 120
gacggcgacg uaaacggcca caaguucagc guguccggcg agggcgaggg cgaugccacc 180
uacggcaagc ugacccugaa guucaucugc accaccggca agcugcccgu gcccuggccc 240
acccucguga ccacccugac cuacggcgug cagugcuuca gccgcuaccc cgaccacaug 300
aagcagcacg acuucuucaa guccgccaug cccgaaggcu acguccagga gcgcaccauc 360
uucuucaagg acgacggcaa cuacaagacc cgcgccgagg ugaaguucga gggcgacacc 420
cuggugaacc gcaucgagcu gaagggcauc gacuucaagg aggacggcaa cauccugggg 480
cacaagcugg aguacaacua caacagccac aacgucuaua ucauggccga caagcagaag 540
aacggcauca aggugaacuu caagauccgc cacaacaucg aggacggcag cgugcagcuc 600
gccgaccacu accagcagaa cacccccauc ggcgacggcc ccgugcugcu gcccgacaac 660
cacuaccuga gcacccaguc cgcccugagc aaagacccca acgagaagcg cgaucacaug 720
guccugcugg aguucgugac cgccgccggg aucacucucg gcauggacga gcuguacaag 780
agaucucaua ugcaucucga gugauagucu agaccuucug cggggcuugc cuucuggcca 840
ugcccuucuu cucucccuug caccuguacc ucuuggucuu ugaauaaagc cugaguagga 900
aaaaaaaaaa aaaaaaaaaa aaaaaaaaaa aaaaaaaaaa aaaaaaaaaa aaaaaaaaaa 960
aaaaaaaaaa aaaaaaaaaa aaaaaaaaaa aaaaaaaaaa aaaaaaaaug uugcgauuau 1020
gaaccuauua gagagaccgg uacccgggga uccucuagag ucgaccugca ggcaugcaag 1080
cuuggcguaa ucauggucau agcuguuucc ugugugaaau uguuauccgc ucacaauucc 1140
acauuuuuuu uuuuuuuuuu uuugaauucu cgcagcccga aga 1183

<210> SEQ ID NO 46
<211> LENGTH: 1143
<212> TYPE: RNA
<213> ORGANISM: Artificial Sequence
<220> FEATURE:
<223> OTHER INFORMATION: EGFP-A109-Tg21-120nt

<400> SEQUENCE: 46
gggcgaauua agagagaaaa gaagaguaag aagaaauaua agacaccggu cgccaccaug 60
ggauccguga gcaagggcga ggagcuguuc accggggugg ugcccauccu ggucgagcug 120
gacggcgacg uaaacggcca caaguucagc guguccggcg agggcgaggg cgaugccacc 180
uacggcaagc ugacccugaa guucaucugc accaccggca agcugcccgu gcccuggccc 240
acccucguga ccacccugac cuacggcgug cagugcuuca gccgcuaccc cgaccacaug 300
aagcagcacg acuucuucaa guccgccaug cccgaaggcu acguccagga gcgcaccauc 360
uucuucaagg acgacggcaa cuacaagacc cgcgccgagg ugaaguucga gggcgacacc 420
cuggugaacc gcaucgagcu gaagggcauc gacuucaagg aggacggcaa cauccugggg 480
cacaagcugg aguacaacua caacagccac aacgucuaua ucauggccga caagcagaag 540

-continued aacggcauca aggugaacuu caagauccgc cacaacaucg aggacggcag cgugcagcuc 600
gccgaccacu accagcagaa cacccccauc ggcgacggcc ccgugcugcu gcccgacaac 660
cacuaccuga gcacccaguc cgcccugagc aaagacccca acgagaagcg cgaucacaug 720
guccugcugg aguucgugac cgccgccggg aucacucucg gcauggacga gcuguacaag 780
agaucucaua ugcaucucga gugauagucu agaccuucug cggggcuugc cuucuggcca 840
ugcccuucuu cucucccuug caccuguacc ucuuggucuu ugaauaaagc cugaguagga 900
aaaaaaaaaa aaaaaaaaaa aaaaaaaaaa aaaaaaaaaa aaaaaaaaaa aaaaaaaaaa 960
aaaaaaaaaa aaaaaaaaaa aaaaaaaaaa aaaaaaaaaa aaaaaaaauu caacaucagu 1020
cugauaagcu aagagaccgg uacccgggga uccucuagag ucgaccugca ggcaugcaag 1080
cuuggcguaa ucauggucau agcuguuucc ugugugaaau uguuauccgc ucacaauucc 1140
aca 1143

<210> SEQ ID NO 47
<211> LENGTH: 1096
<212> TYPE: RNA
<213> ORGANISM: Artificial Sequence
<220> FEATURE:
<223> OTHER INFORMATION: EGFP-A109-Tg21-5UTRcomp20nt

<400> SEQUENCE: 47
gggcgaauua agagagaaaa gaagaguaag aagaaauaua agacaccggu cgccaccaug 60
ggauccguga gcaagggcga ggagcuguuc accggggugg ugcccauccu ggucgagcug 120
gacggcgacg uaaacggcca caaguucagc guguccggcg agggcgaggg cgaugccacc 180
uacggcaagc ugacccugaa guucaucugc accaccggca agcugcccgu gcccuggccc 240
acccucguga ccacccugac cuacggcgug cagugcuuca gccgcuaccc cgaccacaug 300
aagcagcacg acuucuucaa guccgccaug cccgaaggcu acguccagga gcgcaccauc 360
uucuucaagg acgacggcaa cuacaagacc cgcgccgagg ugaaguucga gggcgacacc 420
cuggugaacc gcaucgagcu gaagggcauc gacuucaagg aggacggcaa cauccugggg 480
cacaagcugg aguacaacua caacagccac aacgucuaua ucauggccga caagcagaag 540
aacggcauca aggugaacuu caagauccgc cacaacaucg aggacggcag cgugcagcuc 600
gccgaccacu accagcagaa cacccccauc ggcgacggcc ccgugcugcu gcccgacaac 660
cacuaccuga gcacccaguc cgcccugagc aaagacccca acgagaagcg cgaucacaug 720
guccugcugg aguucgugac cgccgccggg aucacucucg gcauggacga gcuguacaag 780
agaucucaua ugcaucucga gugauagucu agaccuucug cggggcuugc cuucuggcca 840
ugcccuucuu cucucccuug caccuguacc ucuuggucuu ugaauaaagc cugaguagga 900
aaaaaaaaaa aaaaaaaaaa aaaaaaaaaa aaaaaaaaaa aaaaaaaaaa aaaaaaaaaa 960
aaaaaaaaaa aaaaaaaaaa aaaaaaaaaa aaaaaaaaaa aaaaaaaauu caacaucagu 1020
cugauaagcu acauggucau agcuguuucc ugugugauuu cucucuuaau ucgcccgaau 1080
ucucgcagcc cgaaga 1096

<210> SEQ ID NO 48
<211> LENGTH: 1116
<212> TYPE: RNA
<213> ORGANISM: Artificial Sequence
<220> FEATURE:
<223> OTHER INFORMATION: EGFP-A109-Tg21-5UTRcomp40nt

<400> SEQUENCE: 48

```
gggcgaauua agagagaaaa gaagaguaag aagaaauaua agacaccggu cgccaccaug     60
ggauccguga gcaagggcga ggagcuguuc accggggugg ugcccauccu ggucgagcug    120
gacggcgacg uaaacggcca caaguucagc guguccggcg agggcgaggg cgaugccacc    180
uacggcaagc ugacccugaa guucaucugc accaccggca agcugcccgu gcccuggccc    240
acccucguga ccacccugac cuacggcgug cagugcuuca gccgcuaccc cgaccacaug    300
aagcagcacg acuucuucaa guccgccaug cccgaaggcu acguccagga gcgcaccauc    360
uucuucaagg acgacggcaa cuacaagacc cgcgccgagg ugaaguucga gggcgacacc    420
cuggugaacc gcaucgagcu gaagggcauc gacuucaagg aggacggcaa cauccugggg    480
cacaagcugg aguacaacua caacagccac aacgucuaua ucauggccga caagcagaag    540
aacggcauca aggugaacuu caagauccgc cacaacaucg aggacggcag cgugcagcuc    600
gccgaccacu accagcagaa cacccccauc ggcgacggcc ccgugcugcu gcccgacaac    660
cacuaccuga gcacccaguc cgcccugagc aaagacccca acgagaagcg cgaucacaug    720
guccugcugg aguucgugac cgccgccggg aucacucucg gcauggacga gcuguacaag    780
agaucucaua ugcaucucga gugauagucu agaccuucug cggggcuugc cuucuggcca    840
ugcccuucuu cucucccuug caccuguacc ucuuggucuu ugaauaaagc cugaguagga    900
aaaaaaaaaa aaaaaaaaaa aaaaaaaaaa aaaaaaaaaa aaaaaaaaaa aaaaaaaaaa    960
aaaaaaaaaa aaaaaaaaaa aaaaaaaaaa aaaaaaaaaa aaaaaaaauu caacaucagu   1020
cugauaagcu acauggucau agcuguuucc ugugugua uuucuucuua cucuucuuuu   1080
cucucuuaau ucgcccgaau ucucgcagcc cgaaga                              1116
```

```
<210> SEQ ID NO 49
<211> LENGTH: 1120
<212> TYPE: RNA
<213> ORGANISM: Artificial Sequence
<220> FEATURE:
<223> OTHER INFORMATION: EGFP-A109-Tg21-5UTRcomp20nt-stemloop

<400> SEQUENCE: 49
```

```
gggcgaauua agagagaaaa gaagaguaag aagaaauaua agacaccggu cgccaccaug     60
ggauccguga gcaagggcga ggagcuguuc accggggugg ugcccauccu ggucgagcug    120
gacggcgacg uaaacggcca caaguucagc guguccggcg agggcgaggg cgaugccacc    180
uacggcaagc ugacccugaa guucaucugc accaccggca agcugcccgu gcccuggccc    240
acccucguga ccacccugac cuacggcgug cagugcuuca gccgcuaccc cgaccacaug    300
aagcagcacg acuucuucaa guccgccaug cccgaaggcu acguccagga gcgcaccauc    360
uucuucaagg acgacggcaa cuacaagacc cgcgccgagg ugaaguucga gggcgacacc    420
cuggugaacc gcaucgagcu gaagggcauc gacuucaagg aggacggcaa cauccugggg    480
cacaagcugg aguacaacua caacagccac aacgucuaua ucauggccga caagcagaag    540
aacggcauca aggugaacuu caagauccgc cacaacaucg aggacggcag cgugcagcuc    600
gccgaccacu accagcagaa cacccccauc ggcgacggcc ccgugcugcu gcccgacaac    660
cacuaccuga gcacccaguc cgcccugagc aaagacccca acgagaagcg cgaucacaug    720
guccugcugg aguucgugac cgccgccggg aucacucucg gcauggacga gcuguacaag    780
agaucucaua ugcaucucga gugauagucu agaccuucug cggggcuugc cuucuggcca    840
ugcccuucuu cucucccuug caccuguacc ucuuggucuu ugaauaaagc cugaguagga    900
```

```
aaaaaaaaaa aaaaaaaaaa aaaaaaaaaa aaaaaaaaaa aaaaaaaaaa aaaaaaaaaa    960

aaaaaaaaaa aaaaaaaaaa aaaaaaaaaa aaaaaaaaaa aaaaaaaauu caacaucagu   1020

cugauaagcu acauggucau agcuguuucc uguguguuuu cucucuuaau ucgccccgcg   1080

cuggacggga guccagcgcg gaauucucgc agcccgaaga                          1120


<210> SEQ ID NO 50
<211> LENGTH: 1526
<212> TYPE: RNA
<213> ORGANISM: Artificial Sequence
<220> FEATURE:
<223> OTHER INFORMATION: EGFP-A109-Tg21-500nt

<400> SEQUENCE: 50

gggcgaauua agagagaaaa gaagaguaag aagaaauaua agacaccggu cgccaccaug     60

ggauccguga gcaagggcga ggagcuguuc accggggugg ugcccauccu ggucgagcug    120

gacggcgacg uaaacggcca caaguucagc guguccggcg agggcgaggg cgaugccacc    180

uacggcaagc ugacccugaa guucaucugc accaccggca agcugcccgu gcccuggccc    240

acccucguga ccacccugac cuacggcgug cagugcuuca gccgcuaccc cgaccacaug    300

aagcagcacg acuucuucaa guccgccaug cccgaaggcu acguccagga gcgcaccauc    360

uucuucaagg acgacggcaa cuacaagacc cgcgccgagg ugaaguucga gggcgacacc    420

cuggugaacc gcaucgagcu gaagggcauc gacuucaagg aggacggcaa cauccugggg    480

cacaagcugg aguacaacua caacagccac aacgucuaua ucauggccga caagcagaag    540

aacggcauca aggugaacuu caagauccgc cacaacaucg aggacggcag cgugcagcuc    600

gccgaccacu accagcagaa cacccccauc ggcgacggcc ccgugcugcu gcccgacaac    660

cacuaccuga gcacccaguc cgcccugagc aaagacccca acgagaagcg cgaucacaug    720

guccugcugg aguucgugac cgccgccggg aucacucucg gcauggacga gcuguacaag    780

agaucucaua ugcaucucga gugauagucu agaccuucug cggggcuugc cuucuggcca    840

ugcccuucuu cucucccuug caccuguacc ucuuggucuu ugaauaaagc cugaguagga    900

aaaaaaaaaa aaaaaaaaaa aaaaaaaaaa aaaaaaaaaa aaaaaaaaaa aaaaaaaaaa    960

aaaaaaaaaa aaaaaaaaaa aaaaaaaaaa aaaaaaaaaa aaaaaaaauu caacaucagu   1020

cugauaagcu acauggucau agcuguuucc ugugugaaau uguuauccgc ucacaauucc   1080

acacaacaua cgagccggaa gcauaaagug uaaagccugg ggugccuaau gagugagcua   1140

acucacauua auugcguugc gcucacugcc cgcuuuccag ucgggaaacc ugucgugcca   1200

gcugcauuaa ugaaucggcc aacgcgcggg gagaggcggu uugcguauug ggcgcucuuc   1260

cgcuuccucg cucacugacu cgcugcgcuc ggucguucgg cugcggcgag cgguaucagc   1320

ucacucaaag gcggucgcuu ccucgcucac ugacucgcug cgcucggucg uucggcugcg   1380

gcgagcggua ucagcucacu caaaggcggu aauacgguua uccacagaau caggggauaa   1440

cgcaggaaag aacaugugag caaaaggcca gcaaaaggcc aggaaccgua aaaaggccgc   1500

guugcuggcg uuuuuccaua ggcucc                                         1526


<210> SEQ ID NO 51
<211> LENGTH: 2281
<212> TYPE: RNA
<213> ORGANISM: Artificial Sequence
<220> FEATURE:
<223> OTHER INFORMATION: EGFP-A109-Tg21-1250nt

<400> SEQUENCE: 51
```

-continued

```
gggcgaauua agagagaaaa gaagaguaag aagaaauaua agacaccggu cgccaccaug     60
ggauccguga gcaagggcga ggagcuguuc accggggugg ugcccauccu ggucgagcug    120
gacggcgacg uaaacggcca caaguucagc guguccggcg agggcgaggg cgaugccacc    180
uacggcaagc ugacccugaa guucaucugc accaccggca agcugcccgu gcccuggccc    240
acccucguga ccacccugac cuacggcgug cagugcuuca gccgcuaccc cgaccacaug    300
aagcagcacg acuucuucaa guccgccaug cccgaaggcu acguccagga gcgcaccauc    360
uucuucaagg acgacggcaa cuacaagacc cgcgccgagg ugaaguucga gggcgacacc    420
cuggugaacc gcaucgagcu gaagggcauc gacuucaagg aggacggcaa cauccugggg    480
cacaagcugg aguacaacua caacagccac aacgucuaua ucauggccga caagcagaag    540
aacggcauca aggugaacuu caagauccgc cacaacaucg aggacggcag cgugcagcuc    600
gccgaccacu accagcagaa cacccccauc ggcgacggcc ccgugcugcu gcccgacaac    660
cacuaccuga gcacccaguc cgcccugagc aaagacccca acgagaagcg cgaucacaug    720
guccugcugg aguucgugac cgccgccggg aucacucucg gcauggacga gcuguacaag    780
agaucucaua ugcaucucga gugauagucu agaccuucug cggggcuugc cuucuggcca    840
ugcccuucuu cucucccuug caccuguacc ucuuggucuu ugaauaaagc cugaguagga    900
aaaaaaaaaa aaaaaaaaaa aaaaaaaaaa aaaaaaaaaa aaaaaaaaaa aaaaaaaaaa    960
aaaaaaaaaa aaaaaaaaaa aaaaaaaaaa aaaaaaaaaa aaaaaaaauu caacaucagu   1020
cugauaagcu acauggucau agcuguuucc ugugugaaau uguuauccgc ucacaauucc   1080
acacaacaua cgagccggaa gcauaaagug uaaagccugg ggugccuaau gagugagcua   1140
acucacauua auugcguugc gcucacugcc cgcuuuccag ucgggaaacc ugucgugcca   1200
gcugcauuaa ugaaucggcc aacgcgcggg gagaggcggu uugcguauug ggcgcucuuc   1260
cgcuuccucg cucacugacu cgcugcgcuc ggucguucgg cugcggcgag cgguaucagc   1320
ucacucaaag gcggucgcuu ccucgcucac ugacucgcug cgcucggucg uucggcugcg   1380
gcgagcggua ucagcucacu caaaggcggu aauacgguua uccacagaau caggggauaa   1440
cgcaggaaag aacaugugag caaaaggcca gcaaaaggcc aggaaccgua aaaaggccgc   1500
guugcuggcg uuuuuccaua ggcuccgccc cccugacgag caucacaaaa aucgacgcuc   1560
aagucagagg uggcgaaacc cgacaggacu auaaagauac caggcguuuc cccuggaag    1620
cucccucgug cgcucuccug uuccgacccu gccgcuuacc ggauaccugu ccgccuuucu   1680
cccuucggga agcguggcgc uuucucauag cucacgcugu agguaucuca guucggugua   1740
ggucguucgc uccaagcugg gcugugugca cgaacccccc guucagcccg accgcugcgc   1800
cuuauccggu aacuaucguc uugaguccaa cccgguaaga cacgacuuau cgccacuggc   1860
agcagccacu gguaacagga uuagcagagc gagguaugua ggcggugcua cagaguucuu   1920
gaaguggugg ccuaacuacg gcuacacuag aagaacagua uuugguaucu gcgcucugcu   1980
gaagccaguu accuucggaa aaagaguugg uagcucuuga uccggcaaac aaaccaccgc   2040
ugguagcggu gguuuuuuug uuugcaagca gcagauuacg cgcagaaaaa aaggaucuca   2100
agaagauccu uugaucuuuu cuacggguc ugacgcucag uggaacgaaa acucacguua   2160
agggauuuug gucaugagau uaucaaaaag gaucuucacc uagauccuuu uaaauuaaaa   2220
augaaguuuu aaaucaaucu aaaguauaua ugaguaaacu uggucugaca guuaccaaug   2280
c                                                                   2281
```

-continued

```
<210> SEQ ID NO 52
<211> LENGTH: 1120
<212> TYPE: RNA
<213> ORGANISM: Artificial Sequence
<220> FEATURE:
<223> OTHER INFORMATION: miR-302a-5p-respnsive ON-switch mRNA

<400> SEQUENCE: 52

gggcgaauua agagagaaaa gaagaguaag aagaaauaua agacaccggu cgccaccaug     60

ggauccguga gcaagggcga ggagcuguuc accggggugg ugcccauccu ggucgagcug    120

gacggcgacg uaaacggcca caaguucagc guguccggcg agggcgaggg cgaugccacc    180

uacggcaagc ugacccugaa guucaucugc accaccggca agcugcccgu gcccuggccc    240

acccucguga ccacccugac cuacggcgug cagugcuuca gccgcuaccc cgaccacaug    300

aagcagcacg acuucuucaa guccgccaug cccgaaggcu acguccagga gcgcaccauc    360

uucuucaagg acgacggcaa cuacaagacc cgcgccgagg ugaaguucga gggcgacacc    420

cuggugaacc gcaucgagcu gaagggcauc gacuucaagg aggacggcaa cauccugggg    480

cacaagcugg aguacaacua caacagccac aacgucuaua ucauggccga caagcagaag    540

aacggcauca aggugaacuu caagauccgc cacaacaucg aggacggcag cgugcagcuc    600

gccgaccacu accagcagaa cacccccauc ggcgacggcc ccgugcugcu gcccgacaac    660

cacuaccuga gcacccaguc cgcccugagc aaagacccca acgagaagcg cgaucacaug    720

guccugcugg aguucgugac cgccgccggg aucacucucg gcauggacga gcuguacaag    780

agaucucaua ugcaucucga gugauagucu agaccuucug cggggcuugc cuucuggcca    840

ugcccuucuu cucucccuug caccuguacc ucuuggucuu ugaauaaagc cugaguagga    900

aaaaaaaaaa aaaaaaaaaa aaaaaaaaaa aaaaaaaaaa aaaaaaaaaa aaaaaaaaaa    960

aaaaaaaaaa aaaaaaaaaa aaaaaaaaaa aaaaaaaaaa aaaaaaaaag caaguacauc   1020

cacguuuaag ugaucgacuc cguggcacaa uguaacugug uauauuucuu cuuacucuuc   1080

uuuucucucu uaauucgccc gaauucucgc agcccgaaga                         1120
```

METHOD FOR EXPRESSING PROTEIN GENE IN RESPONSE TO EXPRESSION OF MIRNA

RELATED APPLICATIONS

This application is a 35 U.S.C. § 371 national phase application of PCT Application PCT/JP2017/023513 filed Jun. 27, 2017, which claims priority to Japanese Application No. 2016-126982 filed Jun. 27, 2016. The entire contents of each are incorporated herein by reference in its entirety.

FIELD OF THE INVENTION

The present invention relates to a method for expressing a protein gene in response to the expression of a miRNA.

In a cell, miRNA regulates decomposition of the corresponding mRNA, so that the miRNA controls gene expression. It is thought that more than 1800 miRNAs are present in humans. According to recent microarray analysis and the like, the expression level of miRNA is different depending on the types of cells, and thus, it is demonstrated that miRNA can be a parameter for characterizing the cell type or the condition of a cell. Hence, a switch capable of detecting the activity of miRNA in cells and then turning the expression of any given gene ON or OFF, depending on miRNA activity, would be an intelligent gene expression system that responds to the cell type or intracellular environment.

A miRNA-responsive OFF switch, which is a switch responding to miRNA and suppressing gene expression, has been reported based on plasmids (for example, Non Patent Literature 1). In recent years, the present inventors have directly introduced an OFF switch composed of miRNA-responsive mRNA into cells, so that they have reported the expression system of cells that depends on the activity of miRNA and have succeeded in distinguishing the cell type (for example, Patent Literature 1 and Non Patent Literature 2).

A remarkable feature of the OFF switch composed of miRNA-responsive mRNA is that, in principle, insertion into the genome does not take place. Thus, it is thought that the mRNA can be injected into a living body or excised cells can be directly transplanted, and thus, application of the mRNA to medical treatments is anticipated. In addition, because the miRNA-responsive mRNA can be obtained using common PCR and transcription, anyone can conveniently design and produce the mRNA, or it can be useful in that the input miRNA can be replaced with the output gene. As such, the OFF switch composed of miRNA-responsive mRNA is an excellent tool having high versatility and applicability.

CITATION LIST

Patent Literature

Patent Literature 1: International Publication No. WO 2015/105172

Non Patent Literature

Non Patent Literature 1: Rinaudo et al., Nat Biotechnol 2007; 25: 795-801.
Non Patent Literature 2: Miki, K. et al., Cell Stem Cell 16, 699-711 (2015)

SUMMARY OF INVENTION

Technical Problem

A switch, which is based on mRNA, would be highly useful. However, at present, a switch, in which the expression of gene is turned to ON in response to a miRNA has not yet been found. Accordingly, it is impossible, for example, to allow an apoptotic gene to express, targeting to miRNA that activates specifically in cancer cells, so as to specifically kill the cancer cells. On the other hand, it is possible to form a circuit with an OFF switch consisting of a protein-responsive mRNA responding to a specific protein (for example, L7Ae) and another OFF switch consisting of miRNA-responsive mRNA outputting the protein, so as to produce a pseudo-ON switch, in which the expression of L7Ae is suppressed in the presence of a specific miRNA, and as a result, translation suppressed by the L7Ae is finally turned ON. However, such a pseudo-ON switch is seriously problematic in that a large number of constituent elements make the system complicated, in that the expression of a foreign protein is necessary, in that the number of components increases, and thus, uncertainties also increase, in that a plurality of ON switches cannot be simultaneously used, etc.

It has been desired to develop an mRNA-based ON switch, in which the expression is turned ON in response to a miRNA.

Solution to Problem

The present inventors have designed artificial mRNA, in which the structure of the 3'-terminus of mRNA has been modified, and thereby, the present inventors have created an ON switch, in which the expression of a protein is turned ON in response to a miRNA, thereby completing the present invention.

Specifically, the present invention has the following features:

[1] An artificial mRNA comprising a sequence encoding a protein gene, a miRNA target sequence linked to the 3'-terminal side of a Poly A sequence, and a translational repression sequence linked to the 3'-terminal side of the miRNA target sequence.

[2] The artificial mRNA according to [1], wherein the translational repression sequence comprises a sequence selected from (i) a nucleotide sequence consisting of 20 or more nucleotides that specifically recognizes the Poly A sequence, (ii) a sequence specifically recognizing 5' UTR, and (iii) a sequence consisting of 100 or more nucleotides.

[3] A method for expressing a protein gene in response to the expression of a miRNA, which comprises a step of introducing the artificial mRNA according to [1] or [2] into a cell.

[4] A method for determining a desired cell type from a cell group comprising two or more cells, using the expression of a miRNA as an indicator, the method comprising the following steps:

(1) a step of introducing a first artificial mRNA comprising a sequence encoding a first marker gene, a first miRNA target sequence linked to the 3'-terminal side of a Poly A sequence, and a translational repression sequence linked to the 3'-terminal side of the first miRNA target sequence, into the cell group; and (2) a step of determining the cell type, using the translation level of the first marker gene as an indicator.

[5] The method according to [4], wherein
the translational repression sequence comprises a sequence selected from
(i) a nucleotide sequence consisting of 20 or more nucleotides that specifically recognizes the Poly A sequence,
(ii) a sequence specifically recognizing 5' UTR, and
(iii) a sequence consisting of 100 or more nucleotides.
[6] The method according to [5], wherein
the desired cell type is a cell type in which the expression level of the first miRNA is high, and the step (2) is a step of determining a cell type in which the translation level of the first marker gene is high.
[7] The method according to any one of [4] to [6], wherein the first miRNA target sequence comprises a target sequence of miR-302a, and the desired cell type is a pluripotent stem cell.
[8] The method according to any one of [4] to [7], which further comprises:
(3) a step of introducing a second artificial mRNA comprising a second marker gene that is operably linked to a second miRNA target sequence into the cell group, wherein
the second miRNA target sequence is a sequence specifically recognized by the same miRNA as that for the first miRNA target sequence,
the second marker gene is different from the first marker gene,
the second artificial mRNA is an artificial mRNA that reduces the translation level of the second marker gene in response to the expression level of the miRNA.
[9] The method according to any one of [4] to [8], which further comprises:
(4) a step of introducing a third artificial mRNA that does not comprise a miRNA target sequence but comprises a third marker gene into the cell group, wherein
the third marker gene is different from the first and second marker genes, and
the third artificial mRNA translates the third marker gene without being influenced by the expression level of the miRNA.

Advantageous Effects of Invention

According to the present invention, the forced expression of a gene becomes possible in cells in which the activity of a specific miRNA is high, and the gene can be expressed cell-specifically. Moreover, the existing miRNA-responsive OFF switch is used when the activity of a miRNA is low in specific cells, whereas the ON switch of the present invention is used when the miRNA activity is high, so that any given gene can be expressed only in specific cells, depending on a difference in the miRNA activity. By combining the existing OFF switch with the present ON switch, a versatile means for controlling any given gene with respect to any given miRNA in any given direction (forced expression or suppression) can be provided. Examples of specific application of this means include cell separation, induction of differentiation of only specific cells, and the removal of cancer cells by the control of cell death. Since insertion into the genome does not take place as with the OFF switch of miRNA, it is thought that the present ON switch can be applied to medical treatments.

a 20-nt complementary sequence to 5' UTR in the panel (a), a 40-nt complementary sequence to 5' UTR in the panel (b), 20 nt+stem loop in the panel (c), an additional sequence consisting of approximately 120 nt in the panel (d), an additional sequence consisting of approximately 500 nt in the panel (e), and an additional sequence consisting of approximately 1250 nt in the panel (f).

Figure 4:
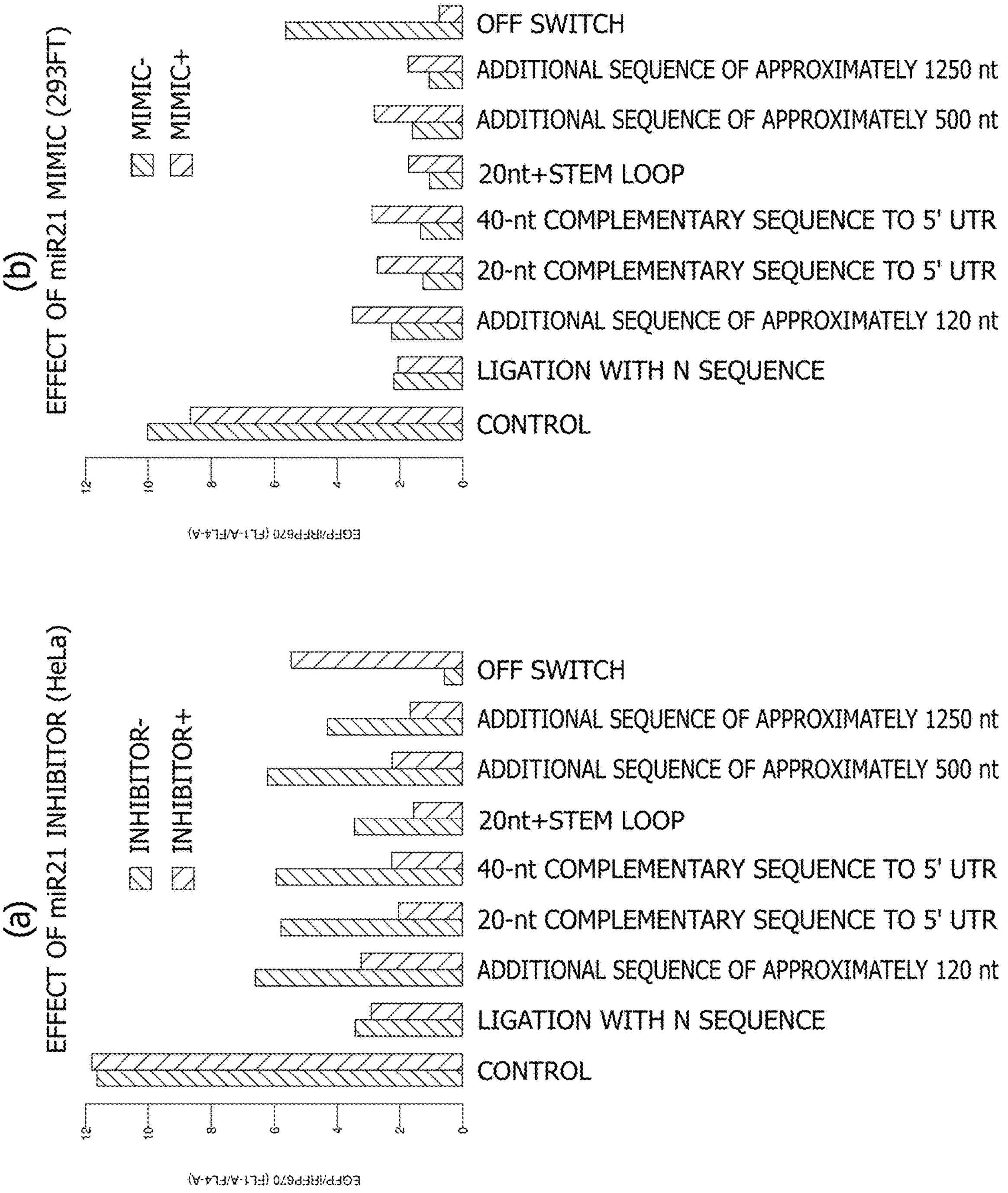

FIG. 4 is a graph showing a change in the expression level of EGFP with respect to a miRNA21 mimic or an inhibitor. The panel (a) shows the expression level of EGFP of an mRNA having a miRNA21 target sequence, in the case of adding (+) or not adding (−) a miRNA21 inhibitor to HeLa cells, and the panel (b) shows the expression level of EGFP of an mRNA having a miRNA21 target sequence, in the case of adding (+) or not adding (−) a miRNA21 mimic to 293FT cells.

Figure 5:
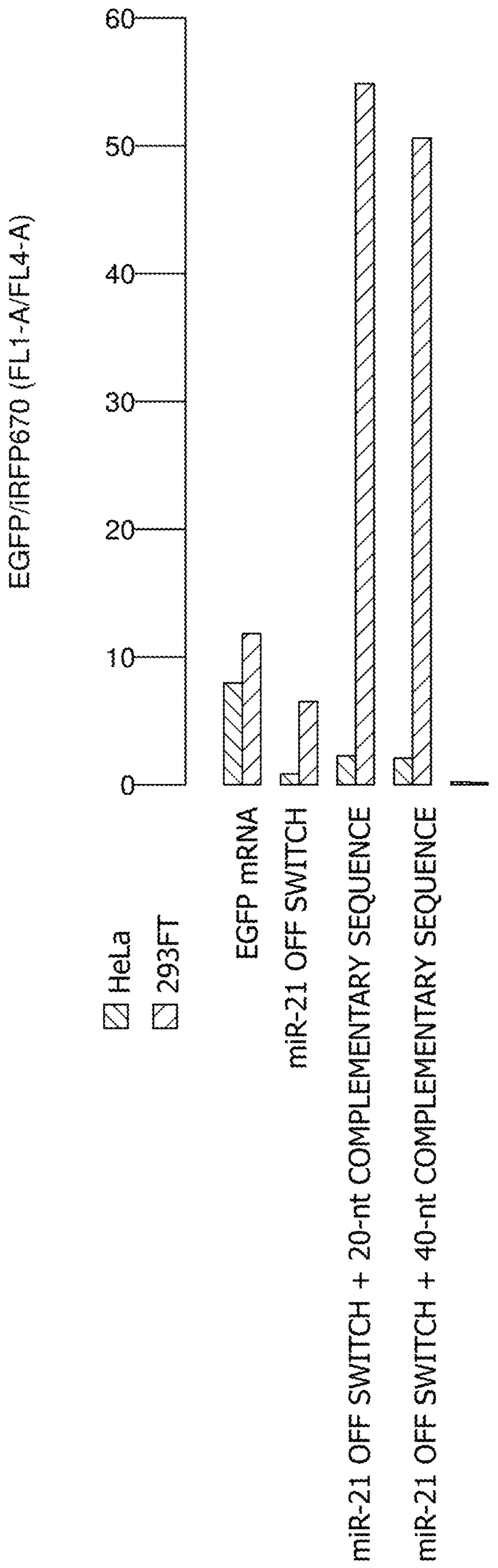

FIG. 5 is a graph showing the improvement of a fold change by a combination of an ON switch with an OFF switch, and the graph shows a fluorescence ratio obtained in the case of introducing mRNAs having various miRNA21 target sequences into HeLa cells or 293F cells.

Figure 6:
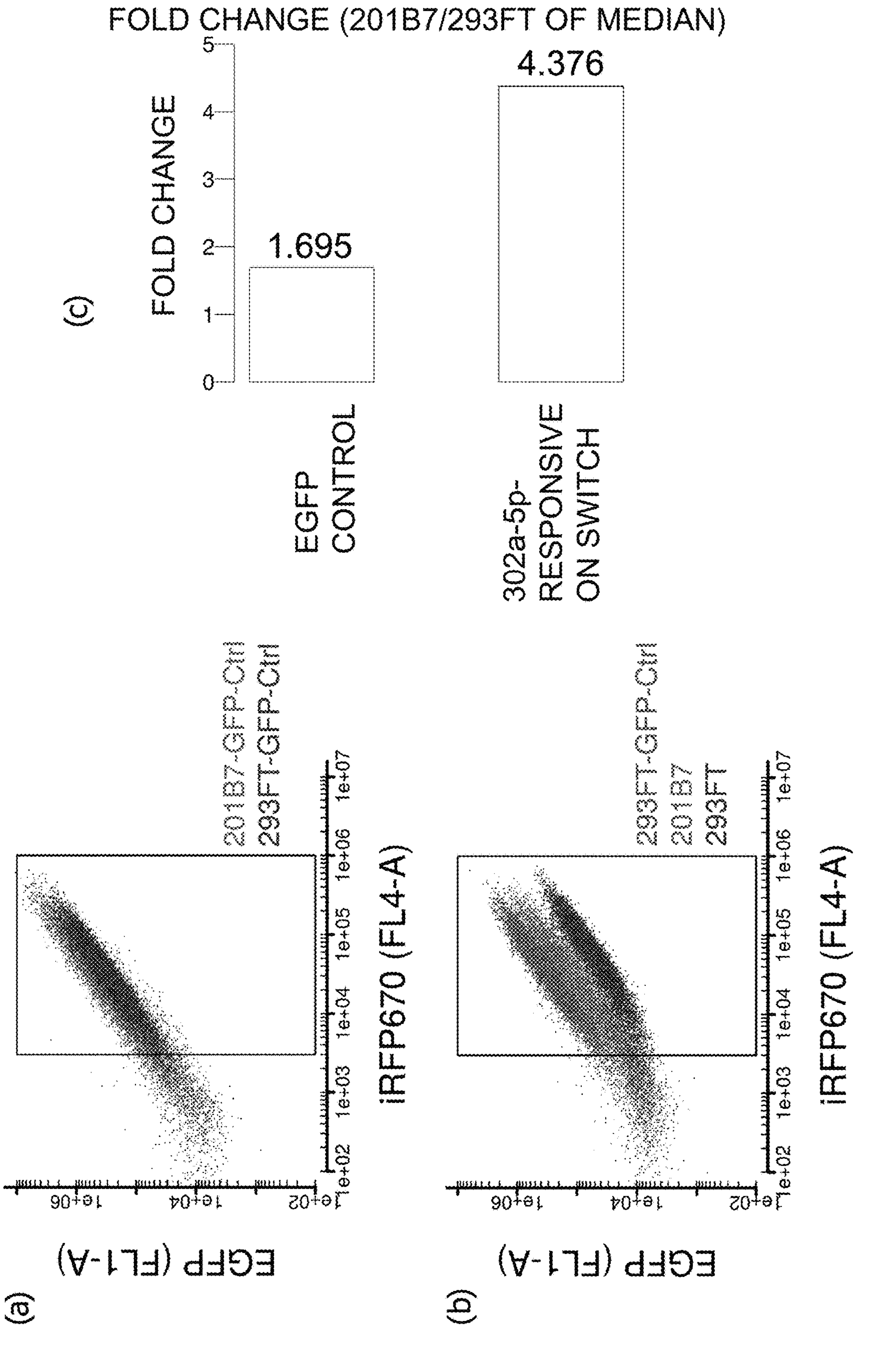

FIG. 6 is a view showing the results of identifying iPS cells by an ON switch having a miR-302a-5p target sequence. The panel (a) shows the fluorescence ratio obtained in the case of co-introducing an OFF switch having a miR-302a-5p target sequence and Control mRNA that does not have a target sequence into HeLa cells and 293F cells, the panel (b) shows the fluorescence ratio obtained in the case of co-introducing an OFF switch having a miR-302a-5p target sequence and an ON switch having a miR-302a-5p target sequence into HeLa cells and 293F cells, and the panel (c) is a graph showing the results obtained by calculating a fold change based on a median of EGFP/iRFP670 in the portion enclosed with the square in each of the panels (a) and (b).

DESCRIPTION OF EMBODIMENTS

Hereinafter, the present invention will be described in detail in the following embodiments. However, the following embodiments are not intended to limit the scope of the present invention.

First Embodiment

According to a first embodiment, the present invention relates to a method for expressing a protein gene in response to the expression of a miRNA, wherein the method comprises a step of introducing an artificial mRNA comprising a sequence encoding a protein gene, a miRNA target sequence linked to the 3'-terminal side of a Poly A sequence, and a translational repression sequence linked to the 3'-terminal side of the miRNA target sequence into cells.

In the present embodiment, as described in detail below, by designing and preparing an artificial mRNA, any given protein can be expressed in response to the expression of any given miRNA, in cells into which the artificial mRNA has been introduced. In the present description, the present artificial mRNA may be referred to as "miRNA-responsive mRNA" or "miRNA-responsive ON-switch mRNA" in some cases.

In the present invention, miRNA is also referred to as microRNA, and it is an RNA 18 to 25 nucleotides in length, which is present in a cell. miRNA means either one strand of a double-stranded RNA generated by cleaving with Dicer, pre-miRNA generated by partially cleaving a pri-mRNA that is a single-stranded RNA transcribed from DNA with an intranuclear enzyme called Drosha. The number of nucleotides constituting a miRNA is, for example, 18 to 25, preferably 20 to 25, and more preferably 21 to 23. A database that stores information of approximately 1,000 miRNAs can be utilized (for example, miRBase). One skilled in the art could extract any given miRNA information from this database, and could readily extract a miRNA that is specifically expressed in cells expressing a protein gene by using the method of the present invention. In addition, the expression of a miRNA means that a miRNA is in a state in which either one strand of the double-stranded RNA cleaved with the aforementioned Dicer interacts with a plurality of predetermined proteins to form an RNA-induced silencing complex (RISK), in cells into which the mRNA according to the present invention is introduced.

In the present invention, for example, a protein gene encoded by the above-described mRNA can be forcibly expressed cell-specifically. The miRNAs specifically expressed in certain cells have been known from the above-described database, publications, etc., and the elucidation thereof is even now continuing. Accordingly, upon designing the above-described mRNA, it is preferable to extract and select a miRNA that is specifically expressed in cells desirably expressing a protein gene.

The cells according to the present embodiment are not particularly limited, as long as they are cells that desirably express a protein gene. Examples of such cells include pluripotent stem cells including induced pluripotent stem (iPS) cells, somatic cells induced to differentiate from the pluripotent stem cells, cells in a process of being induced to differentiate from the pluripotent stem cells, and cancer cells, but are not limited thereto.

When cells into which an mRNA is to be introduced are, for example, pluripotent stem cells, an mRNA that responds to miRNA specifically expressed in pluripotent stem cells can be designed. Such a miRNA specifically expressed in pluripotent stem cells is not particularly limited, as long as it is a miRNA that is known to be specifically expressed in pluripotent stem cells according to publications and the like. For example, such miRNA is either one strand of each of hsa-mir-302a, hsa-mir-302b, hsa-mir-302c, hsa-mir-302d, hsa-mir-367, hsa-5201, hsa-mir-92b, hsa-mir-106a, hsa-mir-18b, hsa-mir-20b, hsa-mir-19b-2, hsa-mir-92a-2, hsa-mir-363, hsa-mir-20a, hsa-mir-17, hsa-mir-18a, hsa-mir-19a, hsa-mir-19b-1, hsa-mir-373, hsa-mir-330, hsa-mir-520c, hsa-mir-182, hsa-mir-183, hsa-mir-96, hsa-mir-92a-1, hsa-mir-92a-2, hsa-mir-141, hsa-mir-200c, hsa-mir-27a, hsa-mir-7-1, hsa-mir-7-2, hsa-mir-7-3, hsa-mir-374a, hsa-mir-106b, hsa-mir-93, hsa-mir-25, hsa-mir-584, hsa-mir-374b, hsa-mir-21, hsa-mir-212, hsa-mir-371a, hsa-mir-371b, hsa-mir-372, hsa-mir-200b, hsa-mir-200a, and hsa-mir-429. Other than these, examples include miRNAs appropriately selected from the miRNAs described in Tobias S. Greve, et al., Annu. Rev. Cell Dev. Biol. 2013. 29: 213-239. The miRNA is preferably either one strand of has-mir-302a or hsa-mir-302b, and more preferably hsa-miR-302b-3p.

In the present invention, the target sequence of a miRNA specifically expressed in cells means a sequence capable of specifically binding to the miRNA. For instance, the miRNA target sequence is preferably a sequence complementary to the miRNA specifically expressed in cells. Otherwise, as long as the miRNA target sequence is recognizable by the miRNA, it may also have a mismatch with the completely complementary sequence. The mismatch with the sequence completely complementary to the miRNA may be generally a mismatch, which is recognizable by the miRNA in a desired cell, and it is thought that there may be a mismatch of approximately 40% to 50% with regard to the original function of the cell in a living body. Such a mismatch is not particularly limited, and it is, for example, a mismatch of 1 nucleotide, 2 nucleotides, 3 nucleotides, 4 nucleotides, 5 nucleotides, 6 nucleotides, 7 nucleotides, 8 nucleotides, 9 nucleotides, 10 nucleotides, or a mismatch of 1%, 5%, 10%, 20%, 30% or 40% of the entire recognition sequence. In addition, in particular, as with the miRNA target sequence on the mRNA contained in a cell, the target sequence may comprise a large number of mismatches in a portion other than a seed region, that is, in a region on the 5'-terminal side in the target sequence, which corresponds to approximately 16 nucleotides on the 3'-terminal side of a miRNA. The seed region may not have such mismatches, or may have a mismatch of 1 nucleotide, 2 nucleotide or 3 nucleotides.

In the present invention, the protein gene encoded by the mRNA may be any given protein gene, and the type of the protein gene is not limited. For instance, the protein gene encoded by the mRNA may be a marker protein gene as described in detail below, or may also be an apoptosis-promoting protein gene, an apoptosis-suppressing protein gene, or a cell surface protein gene.

The marker gene is an RNA sequence encoding any given marker protein, which is translated in a cell, functions as a marker, and enables extraction of differentiated cells, and this RNA sequence can also be referred to as a sequence corresponding to a marker protein. The protein, which is translated in a cell and is able to function as a marker, may be, for example, a protein which can be visualized by fluorescence, luminescence or color development, or by supporting such fluorescence, luminescence or color development, and can be quantified, a membrane-localized protein, or a drug resistance protein, and the like, but the type of the protein is not limited thereto.

Examples of the fluorescent protein include: blue fluorescent proteins such as Sirius or EBFP; cyan fluorescent proteins such as mTurquoise, TagCFP, AmCyan, mTFP1, MidoriishiCyan, or CFP; green fluorescent proteins such as TurboGFP, AcGFP, TagGFP, Azami-Green (e.g. hmAG1), ZsGreen, EmGFP, EGFP, GFP2, or HyPer; yellow fluorescent proteins such as TagYFP, EYFP, Venus, YFP, PhiYFP, PhiYFP-m, TurboYFP, ZsYellow, or mBanana; orange fluorescent proteins such as KusabiraOrange (e.g. hmKO2) or mOrange; red fluorescent proteins such as TurboRFP, DsRed-Express, DsRed2, TagRFP, DsRed-Monomer, AsRed2, or mStrawberry; and near infrared fluorescent proteins such as TurboFP602, mRFP1, JRed, KillerRed, mCherry, HcRed, KeimaRed (e.g. hdKeimaRed), mRasberry, mPlum, or iRFP670, but examples of the fluorescent protein are not limited thereto.

An example of the luminescent protein is aequorin, but examples are not limited thereto. In addition, examples of the protein supporting fluorescence, luminescence or color development include enzymes decomposing fluorescent, luminescent or color development precursors, such as luciferase, phosphatase, peroxidase, or β lactamase, but examples of the type of the protein is not limited thereto. In the present invention, when the substance supporting fluorescence, luminescence or color development is used as a marker, extraction of the differentiated cells is carried out by allowing a cell to come into contact with a corresponding precursor, or by introducing such a corresponding precursor into a cell.

The membrane-localized protein is not particularly limited, as long as it is a membrane-localized protein that is not endogenously expressed in pluripotent stem cells. Examples of the membrane-localized protein include P-gp, MRP1, MRP2 (cMOAT), MRP3, MRP4, MRP5, MRP6, MDR2, and MDR3 proteins. In the present invention, since a membrane-localized protein translated from the introduced mRNA is used as an indicator, a membrane-localized protein that is not endogenously expressed in the target differentiated cells is more preferable. Examples of the drug resistance protein include antibiotic resistance proteins such as a kanamycin resistance protein, an ampicillin resistance protein, a puromycin resistance protein, a blasticidin resistance protein, a gentamycin resistance protein, a kanamycin resistance protein, a tetracycline resistance protein, and a chloramphenicol resistance protein, but are not limited thereto.

Specific examples of the apoptosis-promoting protein gene include Bim-EL, Bax, FADD, and Caspase. Specific examples of the apoptosis-suppressing protein gene include Bcl-xL and Bcl-2. A specific example of the cell surface protein gene is a biotin-added peptide, to which an IgG leader sequence and a PDGFR transmembrane domain are added. However, the protein genes encoded by the mRNA are not limited thereto.

The mRNA preferably comprises, in the direction from the 5'-terminus to the 3'-terminus, a Cap structure (7-methylguanosine 5'-phosphate), an open reading frame encoding a desired protein gene, and a poly A sequence, and also comprises, a miRNA target sequence linked to the 3'-terminal side of the Poly A sequence, and a translational repression sequence linked to the 3'-terminal side of the miRNA target sequence.

The structure of 5' UTR is not particularly limited in terms of the number of nucleotides and the sequence, as long as it comprises a Cap structure but does not comprise a miRNA target sequence at the 5'-terminus thereof. As an example, the structure of 5' UTR is composed of 20 or more nucleotides, and it is composed of, for example, 40 to 150 nucleotides, and preferably approximately 40 to 100 nucleotides. The 5' UTR can be a sequence that hardly has the structure of an RNA such as Stem-loop and does not comprise an initiation codon. However, the 5' UTR is not limited to a specific sequence. The Poly A sequence does not particularly have the upper limit of the length thereof, and it may be a sequence consisting of, for example, 50 to 300 A nucleotides, and preferably 100 to 150 A nucleotides.

The number of miRNA target sequences linked to the 3'-terminal side of the Poly A sequence is preferably 1. This is because, if such a sequence remains on the 3'-terminal side of Poly A after the cleavage of the target sequence by the miRNA, it is hardly recognized as Poly A and the expression of a gene does not start (expression suppression cannot be released) in some cases. However, when the expression suppression can be released after the cleavage of the target sequence by the miRNA, the poly A sequence may comprise a plurality of miRNA target sequences. The phrase "a miRNA target sequence linked to the 3'-terminal side of a Poly A sequence" means that the poly A sequence may be directly linked to the miRNA target sequence, or that the poly A sequence and the miRNA target sequence may comprise a sequence that does not affect their functions, for example, a sequence consisting of approximately 1 to 5 nucleotides, between them.

A translational repression sequence is linked to the 3'-terminal side of the miRNA target sequence. The phrase "a translational repression sequence linked to the 3'-terminal side of the miRNA target sequence" means not only a case in which the miRNA target sequence is directly linked to the translational repression sequence, but also a case in which another sequence may be present between them. For example, the miRNA target sequence and the translational repression sequence may comprise an adapter sequence consisting of 20 to 100 nucleotides between them. Moreover, when two or more miRNA target sequences are contained, "the 3'-terminal side of the miRNA target sequence" means the 3'-terminal side of a miRNA target sequence that is located at the most 3'-terminal side.

The translational repression sequence may be a sequence capable of preventing the action associated with the translation of the Poly A sequence, and the translational repression sequence preferably comprises a nucleotide sequence selected from (i) a nucleotide sequence consisting of 20 or more nucleotides that specifically recognizes the Poly A sequence, (ii) a sequence specifically recognizing 5' UTR, and (iii) a sequence consisting of 100 or more nucleotides.

An example of (i) the nucleotide sequence consisting of 20 or more nucleotides that specifically recognizes the Poly A sequence is a Poly U sequence completely complementary to the Poly A sequence. The Poly U sequence is, for example, a Poly U sequence consisting of 20 or more, 40 or more, 60 or more, or 80 or more uridine nucleotides, but the examples of the Poly U sequence are not limited thereto. Moreover, if the sequence (i) can specifically recognize the Poly A sequence, it may have a mismatch. Furthermore, if the sequence (i) comprises a nucleotide sequence consisting of 20 or more nucleotides, which specifically recognizes the Poly A sequence, it may further comprise any given sequence on the 3'-terminal side and/or 5'-terminal side thereof. In addition, as long as the sequence (i) can specifically recognize the Poly A sequence and can repress the translation thereof, it may not necessarily be a sequence consisting of 20 or more nucleotides, but may be a sequence consisting of 5 or more, 10 or more, or 15 or more nucleotides.

(ii) The sequence specifically recognizing 5' UTR is preferably a sequence completely complementary to 5' UTR. However, if this sequence can specifically recognize 5' UTR, it may have a mismatch with such a completely complementary sequence. Moreover, if the sequence (ii) comprises a sequence specifically recognizing 5' UTR, it may further comprise any given sequence on the 3'-terminal side and/or 5'-terminal side thereof.

(iii) The sequence consisting of 100 or more nucleotides may be a long sequence capable of translational repression, and the types of the nucleotides and the sequence of the nucleotides are not particularly limited. The sequence may consist of 100 or more nucleotides, and may preferably consist of 300 or more nucleotides, 500 or more nucleotides, 1000 or more nucleotides, or 1500 or more nucleotides.

The nucleotides constituting the miRNA-responsive mRNA preferably comprise modified nucleotides such as pseudo uridine and 5-methylcytidine, instead of ordinary uridine and cytidine. This is because of reduction in cytotoxicity. Such modified nucleotides can be positioned independently, as a whole or as a part of the mRNA, in both cases of uridine and cytidine. In the case of being contained as a part, the nucleotides can be positioned randomly at any given ratio.

The miRNA-responsive mRNA having such structural characteristics can hide the poly A sequence from the translation system in cells and can inhibit the translation thereof. It is thought that, in cells, an mRNA is recognized by the CAP structure existing at the 5'-terminus and the poly A sequence existing at the 3'-terminus, and that activation of translation takes place. It is said that the above-designed artificial miRNA-responsive mRNA is temporarily inactivated.

If the miRNA-responsive mRNA is sequenced as described above, it can be synthesized by one skilled in the art according to any method that is already known in the genetic engineering field. In particular, the miRNA-responsive mRNA can be obtained by an in vitro synthesis method using, as a template, template DNA comprising a promoter sequence. One advantage of the present invention is that an mRNA can be obtained as designed according to a simple method.

In the method for expressing a protein gene according to the present invention, only one type of miRNA-responsive mRNA may be introduced into cells, or two or more, for example, three, four, five, six, seven, or eight or more miRNA-responsive mRNAs may be used. The types, numbers, and structures of individual miRNA-responsive mRNAs to be introduced may be designed, as appropriate, by one skilled in the art depending on the purpose of expressing the protein gene. For example, a plurality of miRNA-responsive mRNAs each having a different miRNA target site and an identical protein gene can be designed. Otherwise, a plurality of miRNA-responsive mRNAs each having a different miRNA target site and a different protein gene can also be designed. The translational repression sequences may be identical to or different from one another, as long as they have necessary translation repression function in each miRNA-responsive mRNA.

In the step of introducing a miRNA-responsive mRNA into a cell, one or more miRNA-responsive mRNAs are directly introduced into a cell by using a lipofection method, a liposome method, an electroporation method, a calcium phosphate co-precipitation method, a DEAE dextran method, a microinjection method, a gene gun method, etc. The miRNA-responsive mRNA can also be introduced into a cell in the form of DNA, using a vector or the like. Also in such a case, the same method as that described above can be used. In the case of introduction of two or more different miRNA-responsive mRNAs, a plurality of mRNAs can be co-introduced into a cell, or can also be introduced therein separately. At this time, the amount of miRNA-responsive mRNA introduced is different, depending on the type of cell, into which the mRNA is introduced, the type of the introduced mRNA, a method of introducing the mRNA, and the types of introduction reagents. In order to achieve a desired translation level, one skilled in the art can appropriately select these conditions.

The action of the miRNA-responsive mRNA that has been introduced into a cell will be described. When a miRNA-responsive mRNA is introduced into a certain cell and a miRNA specifically binding to a miRNA target site is present in the cell, the miRNA binds to the miRNA-responsive mRNA and the mRNA is cleaved at a site between the Poly A sequence and the miRNA target site. Thereby, the miRNA-responsive mRNA, which has been temporarily inactivated and the translation of which has been repressed, may be translated, and the expression of a protein gene is initiated and is promoted. When the protein is, for example, a quantitatively measurable marker protein, it can be clearly confirmed that the expression level of the protein shows a correlation with a miRNA in a cell. In addition, such a protein to be expressed may cause cell death or may exhibit predetermined function to cells, depending on the properties of the protein. When a miRNA-responsive mRNA prepared by establishing a plurality of miRNA target sites each binding to different miRNAs in a single mRNA is introduced into a cell, if even one miRNA binding to any of the plurality of miRNA target sites has been expressed in the cell, the translation repression state can be released, and it becomes possible to be translated. On the other hand, when a miRNA specifically binding to such a miRNA target site is not present in the cell, the miRNA-responsive mRNA is not influenced by the miRNA, and thus, the mRNA still remains in the translation repression state. As a result, a protein encoded by the miRNA-responsive mRNA is not expressed, substantially no action takes place, and thus, the miRNA-responsive mRNA is decomposed.

Moreover, when a miRNA-responsive mRNA is introduced into a cell population, in which cells having different properties are present, a protein is expressed only in cells, in which a miRNA specifically binding to a miRNA target site is present, according to the same action as that described above. As a result, cells expressing a predetermined miRNA can be determined based on the expression of the protein, and can be then separated and characterized. The determination of cells using such a miRNA-responsive mRNA will be explained in a second embodiment.

Second Embodiment

According to a second embodiment, the present invention relates to a method for determining a desired cell type from a cell group comprising two or more cells, using the expression of a miRNA as an indicator, the method comprising the following steps:

(1) a step of introducing a first artificial mRNA comprising a sequence encoding a first marker gene, a first miRNA target sequence linked to the 3'-terminal side of a Poly A sequence, and a translational repression sequence linked to the 3'-terminal side of the first miRNA target sequence, into the cell group; and (2) a step of determining the cell type, using the translation level of the first marker gene as an indicator.

In the determination method according to the present embodiment, the cell group used as a target is a cell group comprising two or more cells. This cell group may be either a cell group collected from species of multicellular organisms, or a cell group obtained by culturing isolated cells. The cell group is particularly a cell group comprising two or more somatic cells collected from mammals (e.g., a human, a mouse, a monkey, a swine, a rat, etc.), or a cell group obtained by culturing cells isolated from mammals or mammalian cell lines. Examples of the somatic cells include keratinizing epithelial cells (e.g. keratinized epidermal cells), mucosal epithelial cells (e.g. epithelial cells on a tongue surface layer), exocrine epithelial cells (e.g. mammary gland cells), hormone secreting cells (e.g. adrenomedullary cells), cells for metabolism/storage (e.g. liver cells), inner luminal epithelial cells constituting a boundary surface (e.g. type I alveolar cells), inner luminal epithelial cells in the inner chain tube (e.g. vascular endothelial cells), cells having cilia with transport ability (e.g. respiratory tract epithelial cells), cells for extracellular matrix secretion (e.g. fibroblasts), contractile cells (e.g. smooth muscle cells), cells of blood and immune system (e.g. T lymphocytes), sensory cells (e.g. rod cells), autonomic nervous system neurons (e.g. cholinergic neurons), cells supporting sensory organs and peripheral neurons (e.g. satellite cells), nerve cells and glial cells in the central nervous system (e.g. astroglial cells), pigment cells (e.g. retinal pigment epithelial cells), and the progenitor cells thereof (tissue progenitor cells). The degree of differentiation of cells, the age of an animal from which cells are collected, etc. are not particularly limited. Both undifferentiated progenitor cells (including somatic stem cells) and finally differentiated mature cells can be used as an origin of somatic cells in the present invention. Herein, examples of the undifferentiated progenitor cells include tissue stem cells (somatic stem cells) such as neural stem cells, hematopoietic stem cells, mesenchymal stem cells, or dental pulp stem cells. In the present invention, the type of mammal as the source, from which somatic cells are collected, is not particularly limited, and it is preferably a human. In addition, a preferred cell group is a cell group, in which artificial operations are performed on prophase somatic cells after collection of the cells, and it may be a cell group that includes undesired cells. Thus, the cell group is, for example, a cell group comprising iPS cells prepared from the somatic cells, or a cell group obtained after differentiation of pluripotent stem cells such as ES cells or iPS cells, which may include differentiated cells other than desired cells. In the present embodiment, the cell group as a determination target is preferably in a survival state. In the present invention, the expression “cells in a survival state” is used to mean cells in a state in which they maintain metabolic capacity. The present invention is advantageous in that, after cells have been subjected to the method of the present invention and the determination method has then been terminated, the cells remain alive without losing their original properties, and can be used in the subsequent intended use, in particular, while maintaining division capacity.

In the method of the present invention, the “desired cell type” to be determined means a group of cells, which is classified from other cell types, using the expression of a miRNA as an indicator. In particular, the desired cell type means a certain group of cells having common properties, in terms of miRNA activity, which will be described in detail later. In the present invention, such a certain group of cells, which is classified from other cell types, using miRNA as an indicator, is also referred to as “homologous cells.” The desired cell type determined by the method of the present invention may be one, or two or more, for example, three, four, five, six, seven, or eight or more. Theoretically, the determine-possible cell type is not limited, and according to the present invention, 100 or more cells can be determined simultaneously.

In the present invention, the expression “to determine a desired cell type” is used to mean that the detectable signal information of desired specific one or more cell types, which are different from other cell types, is presented from a cell group comprising two or more cells, and in particular, that visually recognizable information is presented. It is to be noted that the visually recognizable information is not limited to emission of visual signals directly from cells, but it also includes information obtained by converting signals emitted from cells to visually recognizable information, using numerical values, charts, images, etc. Thus, the visually recognizable information means information visually recognizable by one skilled in the art. In the present description, the term “determine” may include the meanings that, after completion of the determination, the desired cell type is recognized, the desired cell type is distinguished, the desired cell type is identified, the desired cell type is classified, the desired cell type is isolated, undesired cell types are removed, the life or death of the desired cell type is determined, specific biological signals are detected or quantified in the desired cell type, and the desired cell type is fractionated based on specific physical or chemical signals. In the present invention, determination whereby a cell group, which has been unknown to comprise two or more types of cells, is determined to comprise different cell types by the method of the present invention, is also considered to be one aspect of determination of a desired cell type.

The first artificial mRNA used in the step (1) according to the present embodiment is the miRNA-responsive ON-switch mRNA described in the first embodiment, in which the protein is a marker protein. In the present embodiment, any given mRNA that functions in response to a miRNA for the forced expression of the protein gene is referred to as a first artificial mRNA.

Upon designing the first artificial mRNA, the marker gene is expressed, and then, a miRNA, which is specifically expressed in desired target cells to be determined, is extracted, and then, a miRNA target site suitable for this miRNA can be selected. Also, a marker gene suitable for the aspect of desired determination can be selected. The type of such a marker gene can be selected from those described in detail in the first embodiment. A preferred marker gene may be a fluorescent protein gene capable of quantitative determination, but it is not limited to a specific marker gene. In the present step, only one first artificial mRNA can be used, or two or more first artificial mRNAs can also be used. In the latter case, a plurality of first artificial mRNAs may be different from one another in terms of the miRNA target site and the marker protein. Otherwise, in some cases, the first artificial mRNAs may be identical to one another in terms of a certain condition. Such first artificial mRNA can be designed, as appropriate, by one skilled in the art, depending on the aspect of determination.

The first artificial mRNA, which has been designed and then prepared according to a genetic engineering means, can be introduced into a cell group by the method described in the first embodiment. At this time, the first artificial mRNA and an mRNA used as a reference (hereinafter also referred to as a “reference mRNA”) can be introduced into such a cell group. The reference mRNA is an mRNA, which can be used to increase separation ability (fold change) in the determination method of the present embodiment, and which behaves specifically or non-specifically to the expression of a miRNA, in a way different from the behavior of the miRNA-responsive ON-switch mRNA.

The reference mRNA may be, for example, a second artificial mRNA comprising a second marker gene, which is operably linked to a second miRNA target sequence. The second artificial mRNA is an artificial mRNA, which reduces the translation level of the second marker gene in response to the expression level of the miRNA, and which is the miRNA-responsive OFF-switch mRNA disclosed in Patent Literature 1 and the like. Regarding this second artificial mRNA, the second miRNA target sequence is a sequence specifically recognized by the same miRNA as that of the first miRNA target sequence. Thus, although the first miRNA target sequence is not necessarily identical to the second miRNA target sequence, they can respond to the same miRNA. Moreover, the second marker gene is different from the aforementioned first marker gene, and signals expressed from these marker genes are separable and distinguishable.

The reference mRNA may also be a third artificial mRNA that does not comprise the target sequence of a miRNA but comprises a third marker gene. The third artificial mRNA is an artificial mRNA, which translates the third marker gene without being influenced by the expression level of the miRNA, and which is the control mRNA disclosed in Patent Literature 1 and the like. Regarding this third artificial mRNA, the third marker gene is different from the first marker gene. In addition, the third marker gene is also different from the second marker gene.

The determination method according to the present embodiment can be carried out only using the first artificial mRNA, or the first and second artificial mRNAs can also be used in combination. All of the first, second, and third artificial mRNAs can also be used. Further, it is also possible to use a plurality of each of the first, second, and third artificial mRNAs.

In the step (1), in the case of using two or more first artificial mRNAs, and/or in the case of using a first artificial mRNA and a reference mRNA, a plurality of mRNAs are preferably co-introduced into a cell group. This is because the ratio of the activities of marker proteins expressed from the thus co-introduced two or more mRNAs is constant in a cell population. At this time, the amount of the mRNA introduced is different, depending on the type of cell group, into which the mRNA is introduced, the type of the introduced mRNA, a method of introducing the mRNA, and the types of introduction reagents. In order to achieve a desired translation level, one skilled in the art can appropriately select these conditions. Also, with regard to the amount of the reference mRNA introduced, in order to achieve a desired translation level, one skilled in the art can appropriately select these conditions.

When the first artificial mRNA is introduced into a cell, the translation of the marker gene encoded by the first artificial mRNA is initiated, if a certain miRNA is present as RISK in the cell. The regulation of the translation level is quantitatively carried out depending on miRNA activity. In contrast, if the certain miRNA is not present in the cell, or if the certain miRNA is not present as RISK, the marker gene encoded by the first artificial mRNA is not translated. Accordingly, the translation level of the marker gene is different between a cell in which the certain miRNA is present as RISK and a cell in which it is not present. It is to be noted that, in the present description, the case where the certain miRNA is present as RISK is also referred to as a "case where miRNA activity is present." On the other hand, the third artificial mRNA, that is, a control mRNA expresses a marker protein, regardless of miRNA activity. This is because, even if such a control mRNA is introduced into a cell, translation is not regulated depending on the expression level of a miRNA, since the miRNA target sequence is not present therein. In the case of the second artificial mRNA, that is, in the case of a miRNA-responsive OFF-switch mRNA, when the certain miRNA is present as RISK in the cell, the translation of a marker gene is suppressed.

Subsequently, a step of determining a cell is carried out, using the translation level of the marker gene in the step (2) as an indicator. In this step, a cell is determined based on the aforementioned translation level of the marker gene. That is, this step can be a step of determining a desired cell type that is a cell in which the expression level of the miRNA used as an indicator is low and the translation level of the marker gene is low, and/or a step of determining a desired cell type that is a cell in which the expression level of the miRNA used as an indicator is high and the translation level of the marker gene is high. Such a cell in which the expression level of the miRNA used as an indicator is low, or a cell in which the expression level of the miRNA used as an indicator is high, can be determined by obtaining the ratio of the translation levels of the marker genes among cells belonging to a cell group comprising two or more cells.

Specifically, the determination step can be carried out by detecting signals from a marker protein, employing a predetermined detection apparatus. Examples of the detection apparatus include a flow cytometer, an imaging cytometer, a fluorescence microscope, a luminescence microscope, and a CCD camera, but examples are not limited thereto. As such a detection apparatus, one skilled in the art can use a suitable apparatus, depending on a marker protein and the mode of determination. For instance, when the marker protein is a fluorescent protein or a luminescent protein, it is possible to quantify the marker protein using a detection apparatus such as a flow cytometer, an imaging cytometer, a fluorescence microscope or a CCD camera. When the marker protein is a protein supporting fluorescence, luminescence or color development, a method of quantifying the marker protein using a detection apparatus such as a luminescence microscope, a CCD camera or a luminometer can be applied. When the marker protein is a membrane localization protein, a method of quantifying the marker protein using a detection reagent specific to a cell surface protein, such as an antibody, and the aforementioned detection apparatus, can be applied, and also, a method of isolating cells without performing the process of quantifying the marker protein, such as a magnetic cell separation device (MACS), can be applied. When the marker protein is a drug resistance gene, a method, which comprises detecting the expression of the marker gene by administration of a drug and then isolating living cells, can be applied.

An example of a preferred detection method, which is applied when the marker protein is a fluorescent protein, is flow cytometry. In the flow cytometry, the intensity of light emitted from a fluorescent protein, luciferase, that is a marker protein translated in each cell, can be provided as information for determination.

In a first aspect of the second embodiment of the present invention, separation and extraction of a predetermined cell group from a cell population, in which undifferentiated cells after completion of the induction of differentiation from pluripotent stem cells are present, will be explained. At this time, the first artificial mRNA can be designed, so that it has a miRNA target sequence that is specifically expressed in pluripotent stem cells. When the first artificial mRNA is introduced into the cell population, the translational repression sequence is cleaved by the expression of the miRNA in the pluripotent stem cells. Then, the first marker gene is expressed and is to be determined. On the other hand, since such a miRNA specifically expressed in pluripotent stem cells is not present as RISK in differentiated cells, the translational repression sequence is not cleaved, and thus, the translation of the first marker gene does not take place. In short, the translation of the marker gene is carried out only in pluripotent stem cells. Accordingly, in one embodiment of the present invention, by extracting cells in which the marker gene has been translated, it becomes possible to selectively extract only pluripotent stem cells from a cell population, in which undifferentiated cells are present after completion of the induction of differentiation from the pluripotent stem cells.

In the step of extracting cells in which the marker gene has been translated, wherein the step may be optionally carried out, the above-described marker gene is translated, and cells, in which the expression of the marker protein has been confirmed, are extracted as pluripotent stem cells. Specifically, the extraction step can be carried out by detecting signals from the marker protein, using a predetermined detection apparatus. Detection of signals from the marker protein may be either digitalization and quantification of the signals or detection of only the presence or absence of the signals. Examples of the detection apparatus include a flow cytometer, an imaging cytometer, a fluorescence microscope, a luminescence microscope, and a CCD camera, but examples are not limited thereto. As such a detection apparatus, one skilled in the art can use a suitable apparatus, depending on the type of a marker protein. For instance, when the marker protein is a fluorescent protein or a luminescent protein, it is possible to confirm the presence or absence of the expression of the marker protein and/or to quantify the marker protein, using a detection apparatus such as a flow cytometer, an imaging cytometer, a fluorescence microscope or a CCD camera. When the marker protein is a protein supporting fluorescence, luminescence or color development, a method of confirming the presence or absence of the expression of the marker protein and/or quantifying the marker protein, using a detection apparatus such as a luminescence microscope, a CCD camera or a luminometer, can be applied. When the marker protein is a membrane localization protein, a method of confirming the presence or absence of the expression of the marker protein and/or quantifying the marker protein, using a detection reagent specific to a cell surface protein, such as an antibody, and the aforementioned detection apparatus, can be applied, and also, a method of isolating cells without performing the process of quantifying the marker protein, such as a magnetic cell separation device (MACS), can be applied. When the marker protein is a drug resistance protein, a method, which comprises detecting the expression of the marker protein by administration of a drug and then isolating living cells, can be applied.

According to a second aspect of the second embodiment, in separation and extraction of a predetermined cell group from a cell population, in which undifferentiated cells are present after completion of the induction of differentiation from pluripotent stem cells, the first artificial mRNA and the second artificial mRNA can be introduced into the cell population. The first and second artificial mRNAs can be designed, so that they have a miRNA target sequence that is specifically expressed in pluripotent stem cells. The first artificial mRNA that has been introduced into the cell population shows the same behavior as that in the previous first aspect. On the other hand, when the second artificial mRNA is introduced into the cell population, the expression of the second marker gene is suppressed by the expression of the miRNA in the pluripotent stem cells, and in differentiated cells, the second marker gene is expressed. Accordingly, cells expressing the first marker gene can be separated as pluripotent stem cells, whereas cells expressing the second marker gene can be separated as undifferentiated cells.

EXAMPLES

Hereinafter, the present invention will be described in more detail in the following examples. However, the following examples are not intended to limit the scope of the present invention.

Experiments

1. Production of PCR Product Having Sequence of EGFP

The sequence of EGFP was obtained by subjecting a plasmid containing a cloned EGFP to PCR, using two synthetic oligo DNAs, namely, TAPEGFPIVTfwd and TAP IVTrev, and then decomposing the plasmid with DpnI. The sequence of 5' UTR was produced by hybridizing synthetic oligo DNAs, that is, IVT 5prime UTR and Rev5UTR, and then elongating the resultant. The sequence of 3'UTR was produced by hybridizing two synthetic oligo DNAs, that is, IVT 3prime UTR and Rev3UTR2T20, and then elongating the resultant. The thus produced EGFPORF, 5' UTR, and 3'UTR were purified, and they were then linked to one another by being subjected to PCR using TAP T7 G3C fwd and Rev3UTR2, which had been mixed and phosphorylated. The PCR product was cloned into a pUC19 vector, thereby producing EGFP comprising UTR (pUC19-EGFPfull). Hereafter, the sequence of EGFP was obtained by performing PCR on this plasmid. The following Table 1 shows the sequences of synthetic oligo DNAs used.

TABLE 1

| Name of Oligo DNA | Sequence (5'→3') | Sequence ID No. |
|---|---|---|
| TAP_IVTrev | GCCCCGCAGAAGGTCTAGACTATCACTCGAGATGCATATGAG ATC | 1 |
| TAPEGFP_ IVTfwd | CACCGGTCGCCACCATGGGATCCGTGAGCAAGGGC | 2 |
| IVT_5prime_ UTR | CAGTGAATTGTAATACGACTCACTATAGGGCGAATTAAGAGA GAAAAGAAGAGTAAGAAGAAATATAAGACACCGGTCGCCACC ATG | 3 |
| Rev5UTR | CATGGTGGCGACCGGTGTCTTATATTTCTTCTTACTC | 4 |
| IVT_3prime_ UTR | TCTAGACCTTCTGCGGGGCTTGCCTTCTGGCCATGCCCTTCTTC TCTCCCTTGCACCTGTACCTCTTGGTCTTTGAATAAAGCCTGAG TAGG | 5 |
| Rev3UTR2T 20 | TTTTTTTTTTTTTTTTTTTTCCTACTCAGGCTTTATTCAAAGACC AAG | 6 |

TABLE 1-continued

| Name of Oligo DNA | Sequence (5'→3') | Sequence ID No. |
|---|---|---|
| TAP_T7_G3C_ fwd_primer | CAGTGAATTGTAATACGACTCACTATAGGGC | 7 |
| Rev3UTR2 | CCTACTCAGGCTTTATTCAAAGACCAAG | 8 |

The produced pUC19-EGFPfull was used as a template, and PCR was then carried out using the primers shown in the following Table 2, each having TAP T7 G3C fwd and the complementary sequence to a miRNA. Poly A and the complementary sequence to a miRNA were added, and thereafter, the plasmid was digested with Dpn I.

TABLE 2

| Name of Oligo DNA | Sequence (5'→3') | Sequence ID No. |
|---|---|---|
| 3UTR-109A-Tg21 (Complementary sequence to miR-21-5p) | tagcttatcagactgatgttgaatttttttttttttttttttttt tttttttttttttttttttttttttttttttttttttttttttt tttttttttttttttttttttttttttttttttttttttcctactc aggctttattc | 9 |
| 3UTR-109A-Tg302 (Complementary sequence to miR-302a-5p) | ACTTAAACGTGGATGTACTTGCTtttttttttttttttttttttt tttttttttttttttttttttttttttttttttttttttttttttt ttttttttttttttttttttttttttttttttttttttcctactcag gctttattc | 10 |
| 3UTR-109A-N | gttgcgattatgaacctattagatttttttttttttttttttttttt ttttttttttttttttttttttttttttttttttttttttttttttt tttttttttttttttttttttttttttttttttttcctactcaggctt tattc | 11 |

2. Production of DNA Template, with 3'-Terminus of Which Additional Sequence is Fused In order to search for a sequence that inhibits translation when added to poly A sequence or later, the following sequences were added. The EGFP having a miRNA-responsive sequence produced in the above 1 was used as a template, and in order to finally unify the 3'-terminus to an M13 sequence or an Rn2 sequence having no complementary sequences on the plasmid, the synthetic oligo DNAs shown in the following Table 3 were used as adapters.

TABLE 3

| Name of Oligo DNA | Sequence (5'→3') | Sequence ID No. |
|---|---|---|
| Tg21-M13NRev (Synthetic oligo DNA adding M13 sequence to complementary sequence to miR-21-5p, used for addition of poly U) | tgtggaattgtgagcggataacaatttcacacaggaaacagctatgaccatgattacgc caagcttgcatgcctgcaggtcgactctagaggatccccgggtaccGGTCTCTt agcttatcagactgatgttgaa | 12 |
| N-Mi3NRev (Synthetic oligo DNA adding M13 sequence to control sequence, used for addition of poly U) | tgtggaattgtgagcggataacaatttcacacaggaaacagctatgaccatgattacgc caagcttgcatgcctgcaggtcgactctagaggatccccgggtaccGGTCTCTg ttgcgattatgaacctattaga | 13 |
| Tg21-M13Rev (Synthetic oligo DNA adding M13 sequence to complementary sequence to miR-21-5p) | cacacaggaaacagctatgaccatgtagcttatcagactgatgttgaattt | 14 |

TABLE 3-continued

| Name of Oligo DNA | Sequence (5'→3') | Sequence ID No. |
|---|---|---|
| N-Mi3Rev (Synthetic oligo DNA adding M13 sequence to control sequence) | cacacaggaaacagctatgaccatggttgcgattatgaacctattagattt | 15 |
| Tg302-M13Rev (Synthetic oligo DNA adding M13 sequence to complementary sequence to miR-302a-5p) | cacacaggaaacagctatgaccatgACTTAAACGTGGATGTACTT GCTttt | 16 |
| Tg21-Rn2-Rev (Synthetic oligo DNA adding Rn2 sequence to complementary sequence to miR-21-5p) | GTTACATTGTGCCACGGAGTCGATCtagcttatcagactgatgtt gaattt | 17 |
| Tg302-Rn2-Rev (Synthetic oligo DNA adding Rn2 sequence to complementary sequence to miR-302a-5p) | GTTACATTGTGCCACGGAGTCGATCACTTAAACGTG GATGTACTTGCTttt | 18 |

Using the M13 sequence or the Rn2 sequence as a joint (adapter sequence), the PCR product having the sequence of EGFP produced in the above 1, the above-described synthetic oligo DNAs, and synthetic oligo DNAs having various sequences were mixed, and the obtained mixture was then subjected to PCR to produce templates for transcription having various 3'-terminus additional sequences. Hereafter, the synthetic oligo DNAs each having a 3'-terminus additional sequence used in the production of templates and the final products (RNAs) are described in terms of only the portions downstream of the poly A sequences. The following Table 4 specifically shows synthetic oligo DNAs having poly U with a length of 80. Other than those, templates having poly U with a length of 20, 40 and 60 were also produced. The dotted line portion indicates an adapter. In the case of using M13, the sequence becomes CAUGGUCAUAGCUGUUUCCUG; in the case of using M13RV, it becomes CCGCUCACAAUUCCACA; and in the case of using Rn2, it becomes GTTACATTGTGCCACGGAGTCGATC. In order to prevent generation of non-specific by-products upon production of such templates, a sequence consisting of GAAUUCUCGCAGCCCGAAGA that is not complementary to the sequences of other regions was added to the 3'-terminus.

Templates, to which a poly U sequence was added, are shown in the following Table 4.

TABLE 4

| Name of Oligo DNA/RNA | Sequence (5' → 3') | Sequence ID No. |
|---|---|---|
| YF549-M13-T20N20 | TCTTCGGGCTGCGAGAATTCaaaaaaaaaaaaaaaaaaaaatgtggaatt gtgagcgg | 19 |
| YF550-M13-T40N20 | TCTTCGGGCTGCGAGAATTCaaaaaaaaaaaaaaaaaaaaaaaaaaaaaa aaaaaaaaaaatgtggaattgtgagegg | 20 |
| YF551-M13-T60N20 | TCTTCGGGCTGCGAGAATTCaaaaaaaaaaaaaaaaaaaaaaaaaaaaaa aaaaaaaaaaaaaaaaaaaaaaaaaaaaaaatgtggaattgtgagegg | 21 |
| YF552-M13-T80N20 | TCTTCGGGCTGCGAGAATTCaaaaaaaaaaaaaaaaaaaaaaaaaaaaaa aaaaaaaaaaaaaaaaaaaaaaaaaaaaaaaaaaaaaaaaaaaaaaaaaa aatgtggaattgtgagegg | 22 |
| Tg21-U80 | UUCAACAUCAGUCUGAUAAGCUAAGAGACCGGUACCCGGGGAUCCUCUA GAGUCGACCUGCAGGCAUGCAAGCUUGGCGUAAUCAUGGUCAUAGCUGU UUCCUGUGUGAAAUUGUUAUCCGCUCACAAUUCCACAUUUUUUUUUUUUU UUUUUUUUUUUUUUUUUUUUUUUUUUUUUUUUUUUUUUUUUUUUUUUUUU UUUUUUUUUUUUUUUUUGAAUUCUCGCAGCCCGAAGA | 23 |

Templates, to which a long chain RNA (approximately 500 or 1200 nt) was added, are shown in the following table, in terms of only the sequence downstream of each poly A sequence. The region of a pGEM-T easy vector was amplified using the following primers and was then bound according to fusion PCR. The dotted line portion in the RNA sequence shown in Table 5 indicates an adapter sequence.

TABLE 5

| Name of Oligo DNA/Name of RNA | Sequence (5' → 3') | Sequence ID No. |
|---|---|---|
| M13Rev-Fwd | catggtcatagctgtttcctgtgtg | 24 |
| M13Rev-1000-Rev | GCATTGGTAACTGTCAGACCAAGTTTACTC | 25 |
| M13Rev-500-Rev | GGAGCCTATGGAAAAACGCCAGCaacg | 26 |
| Additional | UUCAACAUCAGUCUGAUAAGCUACAUGGUCAUAGCUGUUUCCUGUGUG | 27 |
| sequence of approximately 500 nt | AAAUUGUUAUCCGCUCACAAUUCCACACAACAUACGAGCCGGAAGCAU | |
| | AAAGUGUAAAGCCUGGGGUGCCUAAUGAGUGAGCUAACUCACAUUAAU | |
| | UGCGUUGCGCUCACUGCCCGCUUUCCAGUCGGGAAACCUGUCGUGCCA | |
| | GCUGCAUUAAUGAAUCGGCCAACGCGCGGGGAGAGGCGGUUUGCGUAU | |
| | UGGGCGCUCUUCCGCUUCCUCGCUCACUGACUCGCUGCGCUCGGUCGU | |
| | UCGGCUGCGGCGAGCGGUAUCAGCUCACUCAAAGGCGGUCGCUUCCUC | |
| | GCUCACUGACUCGCUGCGCUCGGUCGUUCGGCUGCGGCGAGCGGUAUC | |
| | AGCUCACUCAAAGGCGGUAAUACGGUUAUCCACAGAAUCAGGGGAUAA | |
| | CGCAGGAAAGAACAUGUGAGCAAAAGGCCAGCAAAAGGCCAGGAACCG | |
| | UAAAAAGGCCGCGUUGCUGGCGUUUUUCCAUAGGCUCC | |
| Additional | UUCAACAUCAGUCUGAUAAGCUACAUGGUCAUAGCUGUUUCCUGUGUG | 28 |
| sequence of approximately 1200 nt | AAAUUGUUAUCCGCUCACAAUUCCACACAACAUACGAGCCGGAAGCAU | |
| | AAAGUGUAAAGCCUGGGGUGCCUAAUGAGUGAGCUAACUCACAUUAAU | |
| | UGCGUUGCGCUCACUGCCCGCUUUCCAGUCGGGAAACCUGUCGUGCCA | |
| | GCUGCAUUAAUGAAUCGGCCAACGCGCGGGGAGAGGCGGUUUGCGUAU | |
| | UGGGCGCUCUUCCGCUUCCUCGCUCACUGACUCGCUGCGCUCGGUCGU | |
| | UCGGCUGCGGCGAGCGGUAUCAGCUCACUCAAAGGCGGUCGCUUCCUC | |
| | GCUCACUGACUCGCUGCGCUCGGUCGUUCGGCUGCGGCGAGCGGUAUC | |
| | AGCUCACUCAAAGGCGGUAAUACGGUUAUCCACAGAAUCAGGGGAUAA | |
| | CGCAGGAAAGAACAUGUGAGCAAAAGGCCAGCAAAAGGCCAGGAACCG | |
| | UAAAAAGGCCGCGUUGCUGGCGUUUUUCCAUAGGCUCCGCCCCCCUGA | |
| | CGAGCAUCACAAAAAUCGACGCUCAAGUCAGAGGUGGCGAAACCCGAC | |
| | AGGACUAUAAAGAUACCAGGCGUUUCCCCCUGGAAGCUCCCUCGUGCG | |
| | CUCUCCUGUUCCGACCCUGCCGCUUACCGGAUACCUGUCCGCCUUUCU | |
| | CCCUUCGGGAAGCGUGGCGCUUUCUCAUAGCUCACGCUGUAGGUAUCU | |
| | CAGUUCGGUGUAGGUCGUUCGCUCCAAGCUGGGCUGUGUGCACGAACC | |
| | CCCCGUUCAGCCCGACCGCUGCGCCUUAUCCGGUAACUAUCGUCUUGA | |
| | GUCCAACCCGGUAAGACACGACUUAUCGCCACUGGCAGCAGCCACUGG | |
| | UAACAGGAUUAGCAGAGCGAGGUAUGUAGGCGGUGCUACAGAGUUCUU | |
| | GAAGUGGUGGCCUAACUACGGCUACACUAGAAGAACAGUAUUUGGUAU | |
| | CUGCGCUCUGCUGAAGCCAGUUACCUUCGGAAAAAGAGUUGGUAGCUC | |
| | UUGAUCCGGCAAACAAACCACCGCUGGUAGCGGUGGUUUUUUUGUUUG | |

TABLE 5-continued

| Name of Oligo DNA/Name of RNA | Sequence (5' → 3') | Sequence ID No. |
|---|---|---|
| | CAAGCAGCAGAUUACGCGCAGAAAAAAAGGAUCUCAAGAAGAUCCUUU | |
| | GAUCUUUUCUACGGGGUCUGACGCUCAGUGGAACGAAAACUCACGUUA | |
| | AGGGAUUUUGGUCAUGAGAUUAUCAAAAAGGAUCUUCACCUAGAUCCU | |
| | UUUAAAUUAAAAAUGAAGUUUUAAAUCAAUCUAAAGUAUAUAUGAGUA | |
| | AACUUGGUCUGACAGUUACCAAUGC | |

Additional sequences, to which the complementary sequence to 5' UTR was added, are shown in the following Table 6. In the RNA sequences shown in Table 6, the dotted line portion indicates an adapter sequence, the bold indicates a complementary sequence to 5' UTR, the underlined portion indicates a stem loop, and the 3'-terminus is a sequence that is not complementary to the sequences of other regions.

TABLE 6

| Name of Oligo DNA/Name of RNA | Sequence (5' → 3') | Sequence ID No. |
|---|---|---|
| M13Rev-5Cmp20N20 | TCTTCGGGCTGCGAGAATTCgggcgaattaagagagaaaacacacagg aaacagctatgaccatg | 29 |
| M13Rev-5Cmp40N20 | TCTTCGGGCTGCGAGAATTCgggcgaattaagagagaaaagaagagta agaagaaatatacacacaggaaacagctatgaccatg | 30 |
| M13Rev-5Cmp20SLN20 | TCTTCGGGCTGCGAGAATTCCGCGCTGGACtcccGTCCAGCGCGgggc gaattaagagagaaaacacacaggaaacagctatgaccatg | 31 |
| Additional sequence having 40-nt complementary sequence to 5' UTR (5UTR_Comp40nt) | UUCAACAUCAGUCUGAUAAGCUACAUGGUCAUAGCUGUUUCCUGUGUG **UAUAUUUCUUCUUACUCUUCUUUUCUCUCUUAAUUCGCCC**GAAUUCUC GCAGCCCGAAGA | 32 |
| Additional sequence having 20-nt complementary sequence to 5' UTR (5UTR_Comp20nt) | UUCAACAUCAGUCUGAUAAGCUACAUGGUCAUAGCUGUUUCCUGUGUG **UUUUCUCUCUUAAUUCGCCC**GAAUUCUCGCAGCCCGAAGA | 33 |
| Additional sequence having 20-nt complementary sequence to 5' UTR and a terminus that is a stem loop | UUCAACAUCAGUCUGAUAAGCUACAUGGUCAUAGCUGUUUCCUGUGUG UUUUCUCUCUUAAUUCGCCCCGCGCUGGACGGGAGUCCAGCGCGGAAU UCUCGCAGCCCGAAGA | 34 |

3. Transcription

Transcription was carried out using MEGA shortscript TM T7 Transcription Kit (Thermo Fisher Scientific) in accordance with the instruction manual included therewith. A CAP analog, ARCA, was added to GTP at a ratio of 4:1, and 5-methyl-cytosine and pseudo-uridine were used instead of CTP and UTP, respectively. The transcription scale was set at 10 μL. After completion of the transcription, using DNase I (Thermo Fisher Scientific) and rAPid alkaline phosphatase (Roche), the RNA was subjected to decomposition of the template DNA and dephosphorylation. The reaction was carried out by adding 4 μL of 10×rAPid alkaline phosphatase buffer, 1 μL of rAPid alkaline phosphatase, 0.5 μL of Turbo DNase I, and 40 μL of $H_2O$ to 10 μL of a transcription reaction solution, and then incubating the mixture at 37° C. for 30 minutes. Thereafter, the RNA was purified using RNAeasy MiniElute column (QIAgen) or FavorPrep Blood/Cultured Cells total RNA extraction column (Favorgen Biotech), and was eluted with $H_2O$, followed by measuring the concentration, and the resultant was finally adjusted to 100 ng/μL and was then preserved at −20° C.

4. Introduction into Cells and Quantification of Fluorescence

Cells were seeded on a 24 well plate (HeLa: $0.5\times10^5$, 293FT: $1\times10^5$, iPSC (201B7): $1\times10^5$), and one day later, the medium was replaced with a fresh one before transfection. Transfection of the RNA into the cells was carried out using Stemfect RNA Transfection kit (Stemgent) in accordance with the protocols included therewith. With regard to the amount of the RNA used, 1 μL of Stemfect was used with respect to 100 ng of the mRNA of iRFP670 as an internal control, and with respect to 100 ng of the RNA of an ON switch expressing EGFP. Twelve to twenty-four hours after the introduction, the resulting cells were observed under a fluorescence microscope. Thereafter, the cells were peeled from the plate using Trypsin-EDTA or AccuMax, and then, were fully suspended. The suspension was passed through a mesh to remove large masses. Subsequently, using Accuri C6, the fluorescence of iRFP670 and that of EGFP were quantified, and finally, were quantified by the ratio of EGFP/iRFP670.

The sequence names and sequence numbers of a miRNA-responsive ON-switch mRNA (first artificial mRNA), a miRNA-responsive OFF-switch mRNA (second artificial mRNA), and a control mRNA (third artificial mRNA), which were used in the experiments, are shown in the following Table 7.

TABLE 7

| Name of RNA | Sequence ID No |
|---|---|
| miR21-responsive OFF switch EGFP mRNA | 35 |
| Control EGFP mRNA | 36 |
| Control iRFP670 mRNA | 37 |
| EGFP-A109-Tg21-U80 | 38 |
| EGFP-A109-Tg21-U60 | 39 |
| EGFP-A109-Tg21-U40 | 40 |
| EGFP-A109-Tg21-U20 | 41 |
| EGFP-A109-N-U80 | 42 |
| EGFP-A109-N-U60 | 43 |
| EGFP-A109-N-U40 | 44 |
| EGFP-A109-N-U20 | 45 |
| EGFP-A109-Tg21-120nt | 46 |
| EGFP-A109-Tg21-5UTRcomp20nt | 47 |
| EGFP-A109-Tg21-5UTRcomp40nt | 48 |
| EGFP-A109-Tg21-5UTRcomp20nt-stemloop | 49 |
| EGFP-A109-Tg21-5 00nt | 50 |
| EGFP-A109-Tg21-1250nt | 51 |
| miR-302a-5p-respnsive ON-switch mRNA | 52 |

Results

1. Change in Expression of EGFP in HeLa Cells or 293FT Cells in Case of Linking Poly U with Complementary Sequence to miR-21

Figure 1:
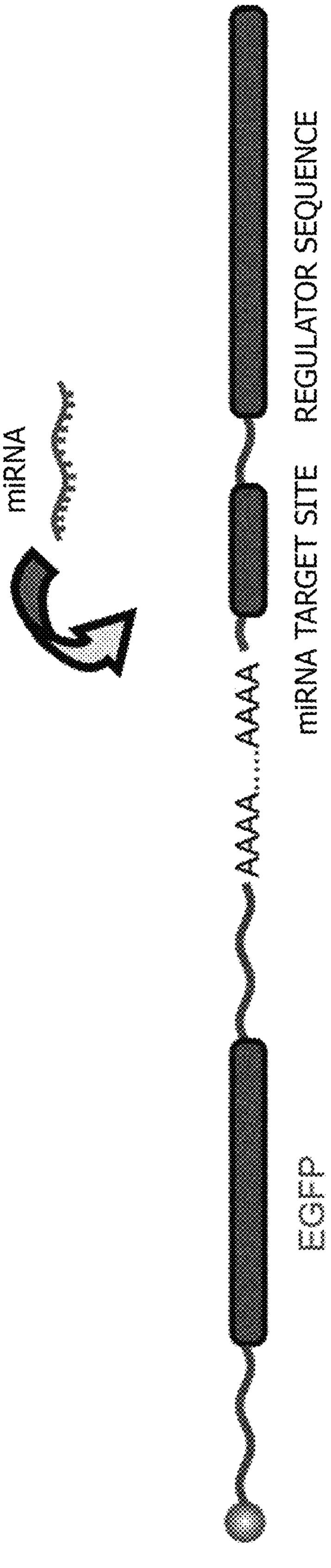
FIG. 1 is a view schematically showing a configuration of the mRNA according to the present invention that expresses a protein gene in response to the expression of a miRNA.
Figure 2:
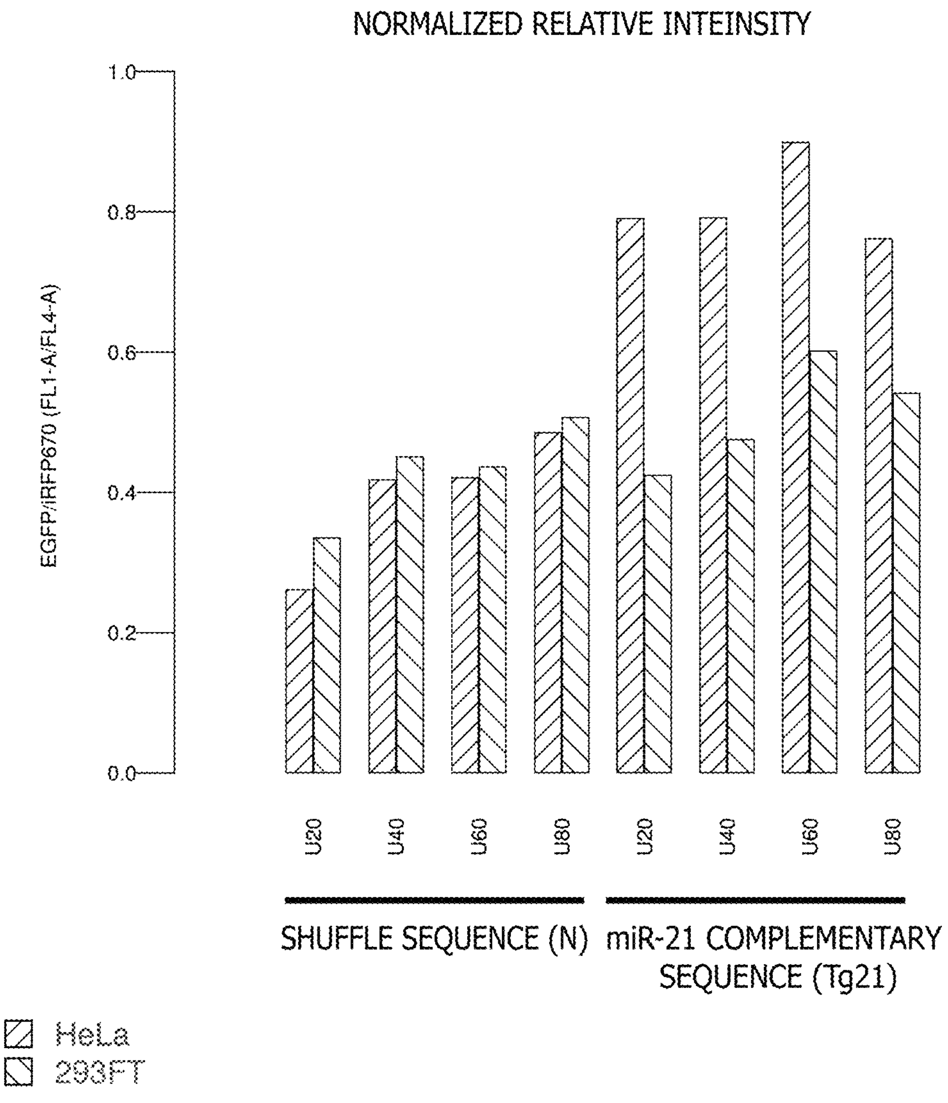
FIG. 2 is a graph showing a change in the expression level of EGFP, which is caused by poly U that is linked downstream of poly A by the complementary sequence (Tg21) to miR-21 or the shuffled sequence (N). Regarding each sequence, the left column shows the results obtained by introduction into HeLa cells and the right column shows the results obtained by introduction into 293FT.

An mRNA, in which poly U had been added to the 3'-terminal side of the poly A of EGFP across the complementary sequence (Tg21) to miR-21 or the sequence (N) obtained by shuffling the complementary sequence to miR-21, was introduced into HeLa cells. Thereafter, the fluorescence of EGFP and the fluorescence of iRFP670 used as a reference were measured with a flow cytometer, and the ratio thereof was then calculated (FIG. 2). As a result, in the case of using the shuffled sequence, almost no change in the ratio was found between the 293FT and HeLa cells. On the other hand, in the case of using the complementary sequence to miR-21, an increase in the fluorescence of EGFP was observed only in the HeLa cells, and thus, it was demonstrated that translation was turned ON in response to miR-21.

2. Change in Expression Level of EGFP in HeLa Cells in Case of Linking Complementary Sequence to 5' UTR with Complementary Sequence to miR-21

Figure 3:
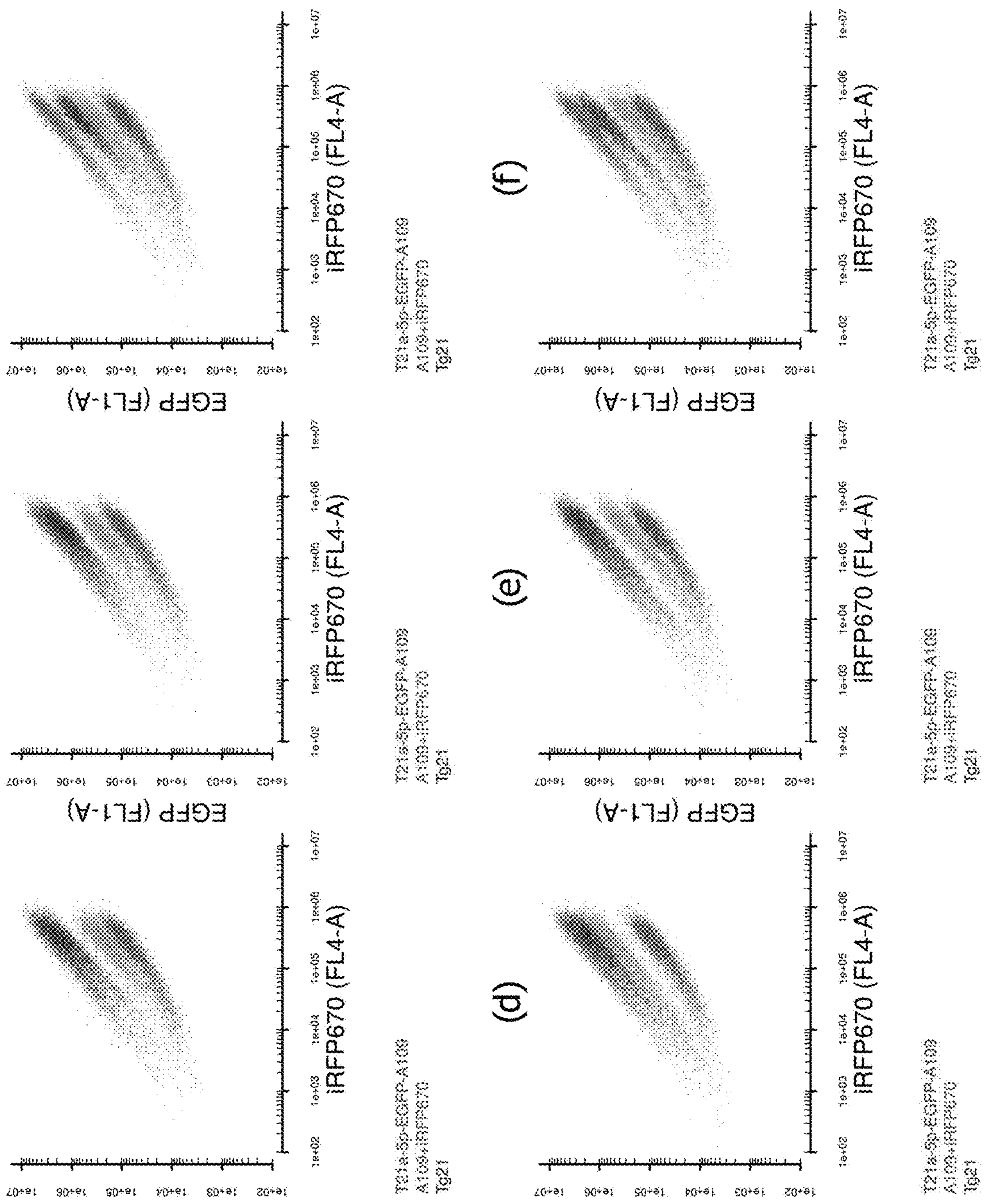
FIG. 3 shows a change in the expression level of EGFP, which is caused by a difference in sequences linked downstream of poly A by the complementary sequence (Tg21) to miR-21 or the shuffled sequence (N). The red indicates a previously produced OFF switch, the green indicates a simple EGFP-expressed mRNA, the light blue indicates a shuffled sequence, and the blue indicates the results of an mRNA comprising a Tg21 sequence. The sequence linked downstream is.

A pGEM-T easy-derived sequence was added to the 3'-terminal side of the poly A of EGFP across the complementary sequence (Tg21) to miR-21 or the sequence (N) obtained by shuffling the complementary sequence to miR-21. On the other hand, HeLa cells, in which miR-21 was highly expressed, were transfected with an mRNA to which the complementary sequence to 5' UTR had been added, and with the mRNA of iRFP670. In these cases, the expression levels of EGFP and iRFP670 were two-dimensionally plotted. The results are shown in FIG. 3. From these results, it was confirmed that the expression level of EGFP is increased in the case of comprising the complementary sequence to miR-21, in comparison to the case of using the N sequence. A large difference was generated between N and Tg21, in particular, in the case of adding the complementary sequence to 5' UTR and the case of adding a long sequence such as a 500-nt sequence, and that the populations are clearly separated from each other.

3. Response of miR-21 to Mimic or Inhibitor in HeLa Cells or 293FT Cells

Using HeLa cells in which miR-21 was highly expressed, and 293FT cells in which miR-21 was not expressed, the response of an mRNA comprising a Tg21 sequence was confirmed. At this time, regarding HeLa cells, the case of adding 2 pmol of inhibitor to the cells and the case of not adding such inhibitor to the cells were subjected to experiments. Regarding 293FT cells, the case of adding 2 pmol of mimic to the cells and the case of not adding such mimic to the cells were subjected to experiments. Regarding the HeLa cells, the results were shown by comparing the case of adding the inhibitor with the case of not adding the inhibitor (FIG. 4(*a*)). Regarding the 293FT cells, the results are shown by comparing the case of adding the mimic with the case of not adding the mimic (FIG. 4(*b*)). As a result, it was confirmed that the expression of the mRNA comprising a Tg21 sequence was decreased by adding the inhibitor to the HeLa cells, that the expression of the mRNA was increased by adding the mimic to the 293FT cells, and that the expression level was increased in response to a miRNA in both cases.

4. Improvement of Separation by Utilizing Reference of ON Switch

A miR-21-responsive iRFP670 ON switch was used as a reference, instead of an iRFP670 mRNA used as a reference of miR-21 OFF switch. It is thought that, since the expression of iRFP670 is suppressed in the absence of miR-21, and thereby the value of EGFP/iRFP670 is increased, the miR-21-expressing cell population is separated from the miR-21-non-expressing cell population. The complementary sequence to 5' UTR used in the above 2 was added to the mRNA of iRFP670 according to the same method as described above, and thereafter, HeLa cells or 293FT cells were transfected with this mRNA and with the miR-21-responsive OFF switch of EGFP. The results are shown in FIG. 5. It was confirmed that, when compared with the single use of the miR-21-responsive OFF switch of EGFP, a difference between ON (HeLa cells) and OFF (293FT cells) is increased in the case of using the miR-21-responsive ON switch of iRFP670 having the 20-nt or 40-nt complementary sequence to 5' UTR.

5. Identification of iPS Cells by Using ON Switch, into Which Complementary Sequence to miR-302a-5p has been Inserted The complementary sequence to miR-21 was replaced with the complementary sequence to miR-302a-5p, so as to produce an mRNA in which the expression of EGFP is increased in response to miR-302a-5p. This mRNA was co-introduced with the mRNA of iRFP670 as a reference into 293FT cells and iPS cells (201B7), and the expression level of fluorescence was then analyzed by flow cytometry. The results are shown in FIG. 6. In the case of a control mRNA of EGFP, which did not contain the complementary sequence to miR-302a-5p, the cell population of 293FT cells and the cell population of iPS cells (201B7) were overlapped with each other. However, in the case of using an ON switch having the complementary sequence to miR-302a-5p, an increase in the fluorescence was observed in iPS cells, and the cell population was separated from the 293FT cells. In addition, it was confirmed that, regarding the median, the value was increased by approximately 4 times in iPS cells, rather than in 293FT cells, and thus, it became clear that a cell population having a specific miRNA can be specifically identified by using the ON switch.

The invention claimed is:

1. An artificial mRNA comprising:

a sequence encoding a protein, a miRNA target sequence linked to the 3'-terminal side of a Poly A sequence of at least 50 nucleotides, and a translational repression sequence linked to the 3'-terminal side of the miRNA target sequence.

2. The artificial mRNA according to claim 1, wherein the translational repression sequence comprises a sequence selected from (i) a nucleotide sequence consisting of 20 or more nucleotides that binds the Poly A sequence in an intracellular environment, (ii) a sequence that binds a 5' UTR in the artificial mRNA in an intracellular environment, and (iii) a sequence consisting of 100 or more nucleotides.

3. A method for expressing a protein in response to the expression of a miRNA, which comprises a step of introducing the artificial mRNA according to claim 1 into a cell.

4. A method for determining a desired cell type from a cell group comprising two or more cells, using the expression of a miRNA as an indicator, the method comprising the following steps:

(1) a step of introducing a first artificial mRNA comprising a sequence encoding a first marker, a first miRNA target sequence linked to the 3'-terminal side of a Poly A sequence of at least 50 nucleotides, and a translational repression sequence linked to the 3'-terminal side of the first miRNA target sequence, into the cell group; and (2) a step of determining the cell type, using the translation level of the first marker as an indicator.

5. The method according to claim 4, wherein the translational repression sequence comprises a sequence selected from (i) a nucleotide sequence consisting of 20 or more nucleotides that binds the Poly A sequence in an intracellular environment, (ii) a sequence that binds a 5' UTR of the first artificial mRNA in an intracellular environment, and (iii) a sequence consisting of 100 or more nucleotides.

6. The method according to claim 5, wherein the desired cell type is a cell type in which the expression level of the first miRNA greater than in other cell types in the cell group, and the step (2) is a step of determining a cell type in which the translation level of the first marker is greater than in other cell types in the cell group.

7. The method according to claim 4, wherein the first miRNA target sequence comprises a target sequence of miR-302a, and the desired cell type is a pluripotent stem cell.

8. The method according to claim 4, which further comprises:

(3) a step of introducing into the cell group a second artificial mRNA encoding a second marker that is different from the first marker and is operably linked to a second miRNA target sequence, wherein the second miRNA target sequence is a sequence that is bound by the same miRNA as that for the first miRNA target sequence in an intracellular environment, and translation of the second marker is inhibited in response to the expression level of the miRNA in the cell group.

9. The method according to claim 8, which further comprises:

(4) a step of introducing into the cell group a third artificial mRNA that does not comprise a miRNA target sequence but encodes a third marker that is different from the first and second markers, wherein translation of the third marker is not influenced by the expression level of the mi RNA in the cell group.

10. A method for expressing a protein in response to the expression of a miRNA, which comprises a step of introducing the artificial mRNA according to claim 2 into a cell.

11. The method according to claim 5, wherein the first miRNA target sequence comprises a target sequence of miR-302a, and the desired cell type is a pluripotent stem cell.

12. The method according to claim 6, wherein the first miRNA target sequence comprises a target sequence of miR-302a, and the desired cell type is a pluripotent stem cell.

13. The method according to claim 5, which further comprises:

(3) a step of introducing into the cell group a second artificial mRNA encoding a second marker that is different from the first marker and is operably linked to a second miRNA target sequence, wherein the second miRNA target sequence is a sequence that is bound by the same miRNA as that for the first miRNA target sequence in an intracellular environment, and translation of the second marker is inhibited in response to the expression level of the miRNA.

14. The method according to claim 6, which further comprises:

(3) a step of introducing into the cell group a second artificial mRNA encoding a second marker that is different from the first marker and is operably linked to a second miRNA target sequence, wherein the second miRNA target sequence is a sequence that is bound by the same miRNA as that for the first miRNA target sequence in an intracellular environment, and translation of the second marker is inhibited in response to the expression level of the miRNA in the cell group.

15. The method according to claim 7, which further comprises:

(3) a step of introducing into the cell group a second artificial mRNA encoding a second marker that is different from the first marker and is operably linked to a second miRNA target sequence, wherein the second miRNA target sequence is a sequence that is bound by the same miRNA as that for the first miRNA target sequence in an intracellular environment, and translation of the second marker is inhibited in response to the expression level of the miRNA in the cell group.

16. The method according to claim 5, which further comprises:

(4) a step of introducing into the cell group a third artificial mRNA that does not comprise a miRNA target sequence but encodes a third marker that is different from the first and second markers, wherein translation of the third marker is not influenced by the expression level of the miRNA in the cell group.

17. The method according to claim 6, which further comprises:

(4) a step of introducing into the cell group a third artificial mRNA that does not comprise a miRNA target sequence but encodes a third marker that is different from the first and second markers, wherein translation of the third marker is not influenced by the expression level of the miRNA in the cell group.

18. The method according to claim 7, which further comprises:

(4) a step of introducing into the cell group a third artificial mRNA that does not comprise a miRNA target sequence but encodes a third marker that is different from the first and second markers, wherein translation of the third marker is not influenced by the expression level of the miRNA in the cell group.

19. The method according to claim 8, which further comprises:

(4) a step of introducing into the cell group a third artificial mRNA that does not comprise a miRNA target sequence but encodes a third marker that is different from the first and second markers, wherein translation of the third marker is not influenced by the expression level of the miRNA in the cell group.

* * * * *

UNITED STATES PATENT AND TRADEMARK OFFICE

CERTIFICATE OF CORRECTION

PATENT NO. : 11,111,503 B2
APPLICATION NO. : 16/313322
DATED : September 7, 2021
INVENTOR(S) : Saito et al.

It is certified that error appears in the above-identified patent and that said Letters Patent is hereby corrected as shown below:

In the Claims

Column 65, Line 23, Claim 9: Please correct "mi RNA" to read -- miRNA --

Signed and Sealed this
First Day of March, 2022

Drew Hirshfeld
*Performing the Functions and Duties of the*
*Under Secretary of Commerce for Intellectual Property and*
*Director of the United States Patent and Trademark Office*